(12) United States Patent
Cortright et al.

(10) Patent No.: US 6,482,611 B1
(45) Date of Patent: Nov. 19, 2002

(54) HUMAN CAPSAICIN RECEPTOR AND USES THEREOF

(75) Inventors: Daniel Cortright, Northford; James Krause, Madison, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/667,422

(22) Filed: Sep. 21, 2000

Related U.S. Application Data

(60) Provisional application No. 60/155,617, filed on Sep. 23, 1999.

(51) Int. Cl.[7] .............................................. C12N 15/12
(52) U.S. Cl. ................ 435/69.1; 435/252.3; 435/320.1; 536/23.5
(58) Field of Search .............................. 435/69.1, 252.3, 435/32.1; 536/23.5

(56) References Cited

U.S. PATENT DOCUMENTS 6,239,267 B1 * 5/2001 Duckworth et al. ....... 536/23.5
6,335,180 B1   1/2002 Julius et al. ................ 435/536

FOREIGN PATENT DOCUMENTS

| WO | WO 99/09140 | 2/1999 |
|---|---|---|
| WO | WO 00/29577 | 5/2000 |
| WO | WO 00/32766 | 6/2000 |
| WO | WO 00/63415 | 10/2000 |

OTHER PUBLICATIONS

Caterina et al. The capsaicin receptor: a heat–activated ion channel in the pain pathway. Oct. 23, 1997. Nature 389:816–824.*

Caterina et al., "The Capsaicin Receptor: a heat activated ion channel in the pain pathway," Nature 389:816–824 (1997).

Caterina et al., "A capsaicin–receptor homologue with a high threshold for noxious heat," Nature 398:436–441 (1999).

* cited by examiner

*Primary Examiner*—John Ulm
(74) *Attorney, Agent, or Firm*—Seth A. Fidel; Leslie-Anne Horvath; Ann T. Kadlecek

(57) ABSTRACT

This invention provides novel human capsaicin receptors and the nucleotide sequences encoding these receptors. Also provided are vectors encoding these receptors and mammalian and non-mammalian cells expressing these vectors. Further provided are assays for identifying compounds that modulate capsaicin receptors and diagnostic assays for capsaicin receptor polymorphisms and aberrant capsaicin receptor expression.

15 Claims, 5 Drawing Sheets

SEQUENCE LISTING

<160> NUMBER OF SEQ ID NOS: 13

<210> SEQ ID NO 1
<211> LENGTH: 4203
<212> TYPE: DNA
<213> ORGANISM: Homo sapiens

<400> SEQUENCE: 1

| | | | | | |
|---|---|---|---|---|---|
| ccgaagggcg | tccacagcga | ctcctgctat | gcagggcagc | tgctgccagg | gccgggcccg | 60 |
| ggaccccacg | gaggcgggga | gaccactctt | ctcccacacg | agcccagctc | tcccttcgag | 120 |
| tagcaaccgc | cttcaagctc | acaagcaccc | gtgggcctgg | ggtgtgcctg | cgtctagctg | 180 |
| gttgcacact | gggccacaga | ggatccagca | aggatgaaga | aatggagcag | cacagacttg | 240 |
| ggggcagctg | cggacccact | ccaaaaggac | acctgcccag | acccctgga | tggagaccct | 300 |
| aactccaggc | cacctccagc | caagccccag | ctctccacgg | ccaagagccg | cacccggctc | 360 |
| tttgggaagg | gtgactcgga | ggaggctttc | ccggtggatt | gccctcacga | ggaaggtgag | 420 |
| ctggactcct | gcccgaccat | cacagtcagc | cctgttatca | ccatccagag | gccaggagac | 480 |
| ggccccaccg | gtgccaggct | gctgtcccag | gactctgtcg | ccgccagcac | cgagaagacc | 540 |
| ctcaggctct | atgatcgcag | gagtatcttt | gaagccgttg | ctcagaataa | ctgccaggat | 600 |
| ctggagagcc | tgctgctctt | cctgcagaag | agcaagaagc | acctcacaga | caacgagttc | 660 |
| aaagaccctg | agacagggaa | gacctgtctg | ctgaaagcca | tgctcaacct | gcacgacgga | 720 |
| cagaacacca | ccatcccccct | gctcctggag | atcgcgcggc | aaacggacag | cctgaaggag | 780 |
| cttgtcaacg | ccagctacac | ggacagctac | tacaagggcc | agacagcact | gcacatcgcc | 840 |
| atcgagagac | gcaacatggc | cctggtgacc | ctcctggtgg | agaacggagc | agacgtccag | 900 |
| gctgcggccc | atgggacttt | ctttaagaaa | accaaagggc | ggcctggatt | ctacttcggt | 960 |
| gaactgcccc | tgtccctggc | cgcgtgcacc | aaccagctgg | gcatcgtgaa | gttcctgctg | 1020 |
| cagaactcct | gcagacggc | cgacatcagc | gccaggact | cggtgggcaa | cacggtgctg | 1080 |
| cacgccctgg | tggaggtggc | cgacaacacg | gccgacaaca | cgaagtttgt | gacgagcatg | 1140 |
| tacaatgaga | ttctgatgct | gggggccaaa | ctgcacccga | cgctgaagct | ggaggagctc | 1200 |
| accaacaaga | agggaatgac | gccgctggct | ctggcagctg | ggaccgggaa | gatcggggtc | 1260 |
| ttggcctata | ttctccagcg | ggagatccag | gagcccgagt | gcaggcacct | gtccaggaag | 1320 |
| ttcaccgagt | gggcctacgg | gcccgtgcac | tcctcgctgt | acgacctgtc | ctgcatcgac | 1380 |
| acctgcgaga | agaactcggt | gctggaggtg | atcgcctaca | gcagcagcga | gacccctaat | 1440 |
| cgccacgaca | tgctcttggt | ggagccgctg | aaccgactcc | tgcaggacaa | gtgggacaga | 1500 |
| ttcgtcaagc | gcatcttcta | cttcaacttc | ctggtctact | gcctgtacat | gatcatcttc | 1560 |
| accatggctg | cctactacag | gcccgtggat | ggcttgcctc | cctttaagat | ggaaaaaatt | 1620 |
| ggagactatt | tccgagttac | tggagagatc | ctgtctgtgt | taggaggagt | ctacttcttt | 1680 |
| ttccgaggga | ttcagtattt | cctgcagagg | cggccgtcga | tgaagaccct | gtttgtggac | 1740 |
| agctacagtg | agatgctttt | ctttctgcag | tcactgttca | tgctggccac | cgtggtgctg | 1800 |
| tacttcagcc | acctcaagga | gtatgtggct | tccatggtat | tctccctggc | cttgggctgg | 1860 |
| accaacatgc | tctactacac | ccgcggtttc | cagcagatgg | gcatctatgc | cgtcatgata | 1920 |
| gagaagatga | tcctgagaga | cctgtgccgt | ttcatgtttg | tctacatcgt | cttcttgttc | 1980 |
| gggttttcca | cagcggtggt | gacgctgatt | gaagacggga | agaatgactc | cctgccgtct | 2040 |

```
gagtccacgt cgcacaggtg gcgggggcct gcctgcaggc cccccgatag ctcctacaac   2100
agcctgtact ccacctgcct ggagctgttc aagttcacca tcggcatggg cgacctggag   2160
ttcactgaga actatgactt caaggctgtc ttcatcatcc tgctgctggc ctatgtaatt   2220
ctcacctaca tcctcctgct caacatgctc atcgccctca tgggtgagac tgtcaacaag   2280
atcgcacagg agagcaagaa catctggaag ctgcagagag ccatcaccat cctggacacg   2340
gagaagagct tccttaagtg catgaggaag gccttccgct caggcaagct gctgcaggtg   2400
gggtacacac ctgatggcaa ggacgactac cggtggtgct tcagggtgga cgaggtgaac   2460
tggaccacct ggaacaccaa cgtgggcatc atcaacgaag acccgggcaa ctgtgagggc   2520
gtcaagcgca ccctgagctt ctccctgcgg tcaagcagag tttcaggcag acactggaag   2580
aactttgccc tggtcccccct tttaagagag gcaagtgctc gagataggca gtctgctcag   2640
cccgaggaag tttatctgcg acagttttca gggtctctga agccagagga cgctgaggtc   2700
ttcaagagtc ctgccgcttc cggggagaag tgaggacgtc acgcagacag cactgtcaac   2760
actgggcctt aggagacccc gttgccacgg gggctgctg agggaacacc agtgctctgt    2820
cagcagcctg gcctggtctg tgcctgccca gcatgttccc aaatctgtgc tggacaagct   2880
gtgggaagcg ttcttggaag catggggagt gatgtacatc caaccgtcat tgtccccaag   2940
tgaatctcct aacagacttt caggttttta ctcactttac taaacagtgt ggatggtcag   3000
tctctactgg gacatgttag gcccttgttt tctttgattt tattctttt tttgagacag    3060 aatttcactc ttctcgccca ggctggaatg cagtggcaca attttggctc cctgcaacct   3120
ccgcctcctg gattccagca attctcctgc ctcggcttcc caagtagctg ggattacagg   3180
cacgtgccac catgtctggc taattttttg tatttttta atagatatgg ggtttcgcca    3240
tgttggccag gctggtctcg aactcctgac ctcaggtgat ccgcccacct cggcctccca   3300
aagtgctggg attacaggtg tgagcctcca cacctggctg ttttctttga ttttattctt   3360
tttttttttt ttctgtgaga cagagtttca ctcttgttgc ccaggctgga gtgcagtggt   3420
gtgatcttgg ctcactgcaa cctctgcctc ccgggttcaa gcgattcttc tgcttcagtc   3480
tcccaagtag cttggattac aggtgagcac taccacgccc ggctaatttt tgtattttta   3540
atagagacgg ggtttcacca tgttggccag gctggtctcg aactcttgac ctcaggtgat   3600
ctgcccgcct ggcctcccca aagtgctggg attacaggtg tgagccgctg cgtcggcct    3660 tctttgattt tatattatta ggagcaaaag taaatgaagc ccaggaaaac acctttggga   3720
acaaactctt cctttgatgg aaaatgcaga ggcccttcct ctctgtgccg tgcttgctcc   3780
tcttacctgc ccgggtggtt tggggtgtt ggtgtttcct ccctggagaa gatggggag    3840 gctgtcccac tcccagctct ggcagaatca agctgttgca gcagtgcctt cttcatcctt   3900
ccttacgatc aatcacagtc tccagaagat cagctcaatt gctgtgcagg ttaaaactac   3960
agaaccacat cccaaaggta cctggtaaga atgtttgaaa gatcttccat ttctaggaac   4020
cccagtcctg cttctccgca atggcacatg cttccactcc atccatactg gcatcctcaa   4080
ataaacagat atgtatwcat ataaaaaaaa aaaaaaaaa aaaaaaaac tcgagagtac     4140 ttctagagcg gccgcgggcc catcgatttt ccacccgggt ggggtaccag gtaaggtgcc   4200
aac                                                               4203

<210> SEQ ID NO 2
<211> LENGTH: 4182
<212> TYPE: DNA
```

<213> ORGANISM: Homo sapiens

<400> SEQUENCE: 2

| | | | | | |
|---|---|---|---|---|---|
| tgctagtgca | gggcagctgc | tgccagggcc | gggcccggga | ccccacggag | gcggggagac | 60 |
| cactcttctc | ccacacgagc | ccagctctcc | cttcgagtag | caaccgcctt | caagctcaca | 120 |
| agcacccgtg | ggcctggggt | gtgcctgcgt | ctagctggtt | gcacactggg | ccacagagga | 180 |
| tccagcaagg | atgaagaaat | ggagcagcac | agacttgggg | gcagctgcgg | acccactcca | 240 |
| aaaggacacc | tgcccagacc | ccctggatgg | agaccctaac | tccaggccac | ctccagccaa | 300 |
| gccccagctc | tccacggcca | agagccgcac | ccggctcttt | gggaagggtg | actcggagga | 360 |
| ggctttcccg | gtggattgcc | ctcacgagga | aggtgagctg | gactcctgcc | cgaccatcac | 420 |
| agtcagccct | gttatcacca | tccagaggcc | aggagacggc | cccaccggtg | ccaggctgct | 480 |
| gtcccaggac | tctgtcgccg | ccagcaccga | aagaccctc | aggctctatg | atcgcaggag | 540 |
| tatctttgaa | gccgttgctc | agaataactg | ccaggatctg | gagagcctgc | tgctcttcct | 600 |
| gcagaagagc | aagaagcacc | tcacagacaa | cgagttcaaa | gaccctgaga | cagggaagac | 660 |
| ctgtctgctg | aaagccatgc | tcaacctgca | cgacggacag | aacaccacca | tccccctgct | 720 |
| cctggagatc | gcgcggcaaa | cggacagcct | gaaggagctt | gtcaacgcca | gctacacgga | 780 |
| cagctactac | aagggccaga | cagcactgca | catcgccatc | gagagacgca | acatggccct | 840 |
| ggtgaccctc | ctggtggaga | acggagcaga | cgtccaggct | gcggcccatg | gggacttctt | 900 |
| taagaaaacc | aagggcggc | ctggattcta | cttcggtgaa | ctgccccctgt | ccctggccgc | 960 |
| gtgcaccaac | cagctgggca | tcgtgaagtt | cctgctgcag | aactcctggc | agacggccga | 1020 |
| catcagcgcc | agggactcgg | tgggcaacac | ggtgctgcac | gccctggtgg | aggtggccga | 1080 |
| caacacggcc | gacaacacga | gtttgtgac | gagcatgtac | aatgagattc | tgatgctggg | 1140 |
| ggccaaactg | cacccgacgc | tgaagctgga | ggagctcacc | aacaagaagg | gaatgacgcc | 1200 |
| gctggctctg | gcagctggga | ccgggaagat | cggggtcttg | gcctatattc | tccagcggga | 1260 |
| gatccaggag | cccgagtgca | ggcacctgtc | caggaagttc | accgagtggg | cctacgggcc | 1320 |
| cgtgcactcc | tcgctgtacg | acctgtcctg | catcgacacc | tgcgagaaga | actcggtgct | 1380 |
| ggaggtgatc | gcctacagca | gcagcgagac | ccctaatcgc | cacgacatgc | tcttggtgga | 1440 |
| gccgctgaac | cgactcctgc | aggacaagtg | ggacagattc | gtcaagcgca | tcttctactt | 1500 |
| caacttcctg | gtctactgcc | tgtacatgat | catcttcacc | atggctgcct | actacaggcc | 1560 |
| cgtggatggc | ttgcctccct | ttaagatgga | aaaaattgga | gactatttcc | gagttactgg | 1620 |
| agagatcctg | tctgtgttag | gaggagtcta | cttcttttc | cgagggattc | agtatttcct | 1680 |
| gcagaggcgg | ccgtcgatga | agaccctgtt | tgtggacagc | tacagtgaga | tgcttttctt | 1740 |
| tctgcagtca | ctgttcatgc | tggccaccgt | ggtgctgtac | ttcagccacc | tcaaggagta | 1800 |
| tgtggcttcc | atggtattct | ccctggcctt | gggctggacc | aacatgctct | actacacccg | 1860 |
| cggtttccag | cagatgggca | tctatgccgt | catgatagag | aagatgatcc | tgagagacct | 1920 |
| gtgccgtttc | atgtttgtct | acatcgtctt | cttgttcggg | ttttccacag | cggtggtgac | 1980 |
| gctgattgaa | gacgggaaga | atgactccct | gccgtctgag | tccacgtcgc | acaggtggcg | 2040 |
| ggggcctgcc | tgcaggcccc | ccgatagctc | ctacaacagc | ctgtactcca | cctgcctgga | 2100 |
| gctgttcaag | ttcaccatcg | gcatgggcga | cctggagttc | actgagaact | atgacttcaa | 2160 |
| ggctgtcttc | atcatcctgc | tgctggccta | tgtaattctc | acctacatcc | tcctgctcaa | 2220 |
| catgctcatc | gccctcatgg | gtgagactgt | caacaagatc | gcacaggaga | gcaagaacat | 2280 |

```
ctggaagctg cagagagcca tcaccatcct ggacacggag aagagcttcc ttaagtgcat   2340
gaggaaggcc ttccgctcag gcaagctgct gcaggtgggg tacacacctg atggcaagga   2400
cgactaccgg tggtgcttca gggtggacga ggtgaactgg accacctgga acaccaacgt   2460
gggcatcatc aacgaagacc cgggcaactg tgagggcgtc aagcgcaccc tgagcttctc   2520
cctgcggtca gcagagtttt caggcagaca ctggaagaac tttgccctgg tccccctttt   2580
aagagaggca agtgctcgag ataggcagtc tgctcagccc gaggaagttt atctgcgaca   2640
gttttcaggg tctctgaagc cagaggacgc tgaggtcttc aagagtcctg ccgcttccgg   2700
ggagaagtga ggacgtcacg cagacagcac tgtcaacact gggccttagg agaccccgtt   2760
gccacggggg gctgctgagg gaacaccagt gctctgtcag cagcctggcc tggtctgtgc   2820
ctgcccagca tgttcccaaa tctgtgctgg acaagctgtg ggaagcgttc ttggaagcat   2880
ggggagtgat gtacatccaa ccgtcactgt ccccaagtga atctcctaac agactttcag   2940
gtttttactc actttactaa acagtgtgga tggtcagtct ctactgggac atgttaggcc   3000
cttgttttct ttgattttat tcttttttttt gagacagaat ttcactcttc tcgcccaggc   3060
tggaatgcag tggcacaatt ttggctccct gcaacctccg cctcctggat tccagcaatt   3120
ctcctgcctc ggcttcccaa gtagctggga ttacaggcac gtgccaccat gtctggctaa   3180 tttttttgtat ttttttaata gatatggggt ttcgccatgt tggccaggct ggtctcgaac   3240
tcctgacctc aggtgatccg cccacctcgg cctcccaaag tgctgggatt acaggtgtga   3300
gcctccacac ctggctgttt tctttgattt tattcttttt tttttttttct gtgagacaga   3360 gtttcactct tgttgcccag gctggagtgc agtggtgtga tcttggctca ctgcaacctc   3420
tgcctcccgg gttcaagcga ttcttctgct tcagtctccc aagtagcttg gattacaggt   3480
gagcactacc acgcccggct aattttttgta tttttaatag agacgggggtt tcaccatgtt   3540 ggccaggctg gtctcgaact cttgacctcg ggtgatctgc ccgccttggc ctcccaaagt   3600
gctgggatta caggtgtgag ccgctgcgct cggccttctt tgattttata ttattaggag   3660
caaaagtaaa tgaagcccag gaaaacacct ttgggaacaa actcttcctt tgatggaaaa   3720
tgcagaggcc cttcctctct gtgccgtgct tgctcctctt acctgcccgg gtggtttggg   3780
ggtgttggtg tttcctcccct ggagaagatg ggggaggctg tcccactccc agctctggca   3840
gaatcaagct gttgcagcag tgccttcttc atccttcctt acgatcaatc acagtctcca   3900
gaagatcagc tcaattgctg tgcaggttaa aactacagaa ccacatccca aaggtacctg   3960
gtaagaatgt ttgaaagatc ttccatttct aggaacccca gtcctgcttc tccgcaatgg   4020
cacatgcttc cactccatcc atactggcat cctcaaaataa acagatatgt atacatataa   4080
aaaaaaaaaa aaaaaaaaaa aaaactcga gagtacttct agagcggccg cgggcccatc   4140 gatttttccac ccgggtgggg taccaggtaa gtgtacccaa tc                     4182
```

<210> SEQ ID NO 3  
<211> LENGTH: 4171  
<212> TYPE: DNA  
<213> ORGANISM: Homo sapiens

<400> SEQUENCE: 3

```
gcagagtgtg cagtatagat tcagcgtttg tcgactgact gaatgatagc acaatccagg     60
ctgcttcctg ttggctgggt ttggttggac tgggacccgt cagaggaaaa ggcaacgccg   120
ctgacaaaga acattgccga aaggttcatg ggaggctccg gctaacaggt tgcacactgg   180
```

-continued

| | |
|---|---|
| gccacagagg atccagcaag gatgaagaaa tggagcagca cagacttggg ggcagctgcg | 240 |
| gacccactcc aaaaggacac ctgcccagac ccctggatg gagaccctaa ctccaggcca | 300 |
| cctccagcca agccccagct ctccacggcc aagagccgca cccggctctt tgggaagggt | 360 |
| gactcggagg aggctttccc ggtggattgc cctcacgagg aaggtgagct ggactcctgc | 420 |
| ccgaccatca cagtcagccc tgttatcacc atccagaggc caggagacgg ctccaccggt | 480 |
| gccaggctgc tgtcccagga ctctgtcgcc gccagcaccg agaagaccct caggctctat | 540 |
| gatcgcagga gtatctttga agccgttgct cagaataact gccaggatct ggagagcctg | 600 |
| ctgctcttcc tgcagaagag caagaagcac ctcacagaca acgagttcaa agaccctgag | 660 |
| acagggaaga cctgtctgct gaaagccatg ctcaacctgc atgacggaca gaacaccacc | 720 |
| atcccctgc tcctggagat cgcgcggcaa acggacagcc tgaaggagct tgtcaacgcc | 780 |
| agctacacgg acagctacta caagggccag acagcactgc acatcgccat cgagagacgc | 840 |
| aacatggccc tggtgaccct cctggtggag aacggagcag acgtccaggc tgcggcccat | 900 |
| ggggacttct ttaagaaaac caagggcgg cctggattct acttcggtga actgcccctg | 960 |
| tccctggccc cgtgcaccaa ccagctgggc atcgtgaagt tcctgctgca gaactcctgg | 1020 |
| cagacgccg acatcagcgc cagggactcg gtgggcaaca cggtgctgca cgccctggtg | 1080 |
| gaggtggccg acaacacggc cgacaacacg aagtttgtga cgagcatgta caatgagatt | 1140 |
| ctgatcctgg gggccaaact gcacccgacg ctgaagctgg aggagctcac caacaagaag | 1200 |
| ggaatgacgc cgctggctct ggcagctggg accgggaaga tcgggtcttt ggcctatatt | 1260 |
| ctccagcggg agatccagga gcccgagtgc aggcacctgt ccaggaagtt caccgagtgg | 1320 |
| gcctacgggc ccgtgcactc ctcgctgtac gacctgtcct gcatcgacac ctgcgagaag | 1380 |
| aactcggtgc tggaggtgat cgcctacagc agcagcgaga cccctaatcg ccacgacatg | 1440 |
| ctcttggtgg agccgctgaa ccgactcctg caggacaagt gggacagatt cgtcaagcgc | 1500 |
| atcttctact tcaacttcct ggtctactgc ctgtacatga tcatcttcac catggctgcc | 1560 |
| tactacaggc ccgtggatgg cttgcctccc tttaagatgg aaaaaattgg agactatttc | 1620 |
| cgagttactg gagagatcct gtctgtgtta ggaggagtct acttctttt ccgagggatt | 1680 |
| cagtatttcc tgcaggcggc cgtcgatgaa gaccctgttt gtggacagct acagtgagat | 1740 |
| gcttttcttt ctgcagtcac tgttcatgct ggccaccgtg gtgctgtact cagccacct | 1800 |
| caaggagtat gtggcttcca tggtattctc cctggccttg gctggacca acatgctcta | 1860 |
| ctacacccgc ggtttccagc agatgggcat ctatgccgtc atgatagaga gatgatcct | 1920 |
| gagagacctg tgccgtttca tgtttgtcta catcgtcttc ttgttcgggt tttccacagc | 1980 |
| ggtggtgacg ctgattgaag acgggaagaa tgactccctg ccgtctgagt ccacgtcgca | 2040 |
| caggtggcgg gggcctgcct gcaggccccc cgatagctcc tacaacagcc tgtactccac | 2100 |
| ctgcctggag ctgttcaagt tcaccatcgg catgggcgac ctggagttca ctgagaacta | 2160 |
| tgacttcaag gctgtcttca tcatcctgct gctggcctat gtaattctca cctacatcct | 2220 |
| cctgctcaac atgctcatcg ccctcatggg tgagactgtc aacaagatcg cacaggagag | 2280 |
| caagaacatc tggaagctgc agagagccat caccatcctg gacacggaga gagcttcct | 2340 |
| taagtgcatg aggaaggcct tccgctcagg caagctgctg caggtggggt acacacctga | 2400 |
| tggcaaggac gactaccggt ggtgcttcag ggtggacgag gtgaactgga ccacctggaa | 2460 |
| caccaacgtg ggcatcatca cgaagaccc gggcaactgt gagggcgtca gcgcaccct | 2520 |
| gagcttctcc ctgcggtcaa gcagagtttc aggcagacac tggaagaact ttgccctggt | 2580 |

-continued

```
ccccctttta agagaggcaa gtgctcgaga taggcagtct gctcagcccg aggaagttta      2640
tctgcgacag ttttcagggt ctctgaagcc agaggacgct gaggtcttca agagtcctgc      2700
cgcttccggg gagaagtgag gacgtcacgc agacagcact gtcaacactg ggccttagga      2760
gaccccgttg ccacgggggg ctgctgaggg aacaccagtg ctctgtcagc agcctggcct      2820
ggtctgtgcc tgcccagcat gttcccaaat ctgtgctgga caagctgtgg gaagcgttct      2880
tggaagcatg gggagtgatg tacatccaac cgtcactgtc cccaagtgaa tctcctaaca      2940
gactttcagg tttttactca ctttactaaa cagtttggat ggtcagtctc tactgggaca      3000
tgttaggccc ttgttttctt tgattttatt cttttttttg agacagaatt tcactcttct      3060
cacccaggct ggaatgcagt ggcacaattt tggctccctg caacctccgc ctcctggatt      3120
ccagcaattc tcctgcctcg gcttcccaag tagctgggat tacaggcacg tgccaccatg      3180
tctggctaat ttttttgtatt ttttaatag atatgggggt tcgccatgtt ggccaggctg      3240
gtctcgaact cctgacctca ggtgatccgc ccacctcggc ctcccaaagt gctgggatta      3300
caggtgtgag cctccacacc tggctgtttt ctttgatttt attctttttt ttttttttctg      3360 tgagacagag tttcactctt gttgcccagg ctggagtgca gtggtgtgat cttggctcac      3420
tgcaacctct gcctcccggg ttcaagcgat tcttctgctt cagtctccca gtagccttgg      3480
attacaggtg agcactacca cgcccggcta attttttgtat ttttaataga cacggggttt      3540
caccatgttg gccaggctgg tctcgaactc ttgacctcag gtgatctgcc cgccttggcc      3600
tcccaaagtg ctgggattac aggtgtgagc tgctgcgctc ggccttcttt gattttatat      3660
tattaggagc aaaagtaaat gaagcccagg aaaacacctt tgggaacaaa ctcttccttt      3720
gatggaaaat gcagaggccc ttcctctctg tgccgtgctt gctcctctta cctgcccggg      3780
tggtttgggg gtgttggtgt ttcctccctg gagaagatgg gggaggctgt cccactccca      3840
gctctggcag aatcaagctg ttgcagcagt gccttcttca tccttcctta cgatcaatca      3900
cagtctccag aagatcagct caattgctgt gcaggttaaa actacagaac cacatcccaa      3960
aggtacctgg taagaatgtt tgaaagatct tccatttcta ggaaccccag tcctgcttct      4020
ccgcaatggc acatgcttcc actccatcca tactggcatc ctcaaataaa cagatatgta      4080
tacataaaaa aaaaaaaaaa aaactcgaga gtacttctag agcggccgcg ggcccatcga      4140
ttttccaccc gggtgggggta ccaggtaagt g                                    4171
```

```
<210> SEQ ID NO 4
<211> LENGTH: 839
<212> TYPE: PRT
<213> ORGANISM: Homo sapiens
<220> FEATURE:
<221> NAME/KEY: TRANSMEM
<222> LOCATION: (434)..(455)
<223> OTHER INFORMATION: TM1
<221> NAME/KEY: TRANSMEM
<222> LOCATION: (480)..(495)
<223> OTHER INFORMATION: TM2
<221> NAME/KEY: TRANSMEM
<222> LOCATION: (510)..(530)
<223> OTHER INFORMATION: TM3
<221> NAME/KEY: TRANSMEM
<222> LOCATION: (543)..(569)
<223> OTHER INFORMATION: TM4
<221> NAME/KEY: TRANSMEM
<222> LOCATION: (577)..(596)
<223> OTHER INFORMATION: TM5
<221> NAME/KEY: TRANSMEM
<222> LOCATION: (656)..(684)
<223> OTHER INFORMATION: TM6
```

-continued

```
<400> SEQUENCE: 4

Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Ala Phe Pro Val Asp Cys Pro
        50                  55                  60

His Glu Glu Gly Glu Leu Asp Ser Cys Pro Thr Ile Thr Val Ser Pro
 65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
            115                 120                 125

Asp Leu Glu Ser Leu Leu Leu Phe Leu Gln Lys Ser Lys Lys His Leu
            130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
            195                 200                 205

Ala Ile Glu Arg Arg Asn Met Ala Leu Val Thr Leu Leu Val Glu Asn
            210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
            275                 280                 285

Leu His Ala Leu Val Glu Val Ala Asp Asn Thr Ala Asp Asn Thr Lys
            290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
            355                 360                 365

Lys Phe Thr Glu Trp Ala Tyr Gly Pro Val His Ser Ser Leu Tyr Asp
        370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
```

-continued

```
                    405                 410                 415
    Glu Pro Leu Asn Arg Leu Leu Gln Asp Lys Trp Asp Arg Phe Val Lys
                    420                 425                 430
    Arg Ile Phe Tyr Phe Asn Phe Leu Val Tyr Cys Leu Tyr Met Ile Ile
                    435                 440                 445
    Phe Thr Met Ala Ala Tyr Tyr Arg Pro Val Asp Gly Leu Pro Pro Phe
                    450                 455                 460
    Lys Met Glu Lys Ile Gly Asp Tyr Phe Arg Val Thr Gly Glu Ile Leu
    465                 470                 475                 480
    Ser Val Leu Gly Gly Val Tyr Phe Phe Arg Gly Ile Gln Tyr Phe
                        485                 490                 495
    Leu Gln Arg Arg Pro Ser Met Lys Thr Leu Phe Val Asp Ser Tyr Ser
                    500                 505                 510
    Glu Met Leu Phe Phe Leu Gln Ser Leu Phe Met Leu Ala Thr Val Val
                    515                 520                 525
    Leu Tyr Phe Ser His Leu Lys Glu Tyr Val Ala Ser Met Val Phe Ser
                    530                 535                 540
    Leu Ala Leu Gly Trp Thr Asn Met Leu Tyr Tyr Thr Arg Gly Phe Gln
    545                 550                 555                 560
    Gln Met Gly Ile Tyr Ala Val Met Ile Glu Lys Met Ile Leu Arg Asp
                        565                 570                 575
    Leu Cys Arg Phe Met Phe Val Tyr Ile Val Phe Leu Phe Gly Phe Ser
                    580                 585                 590
    Thr Ala Val Val Thr Leu Ile Glu Asp Gly Lys Asn Asp Ser Leu Pro
                    595                 600                 605
    Ser Glu Ser Thr Ser His Arg Trp Arg Gly Pro Ala Cys Arg Pro Pro
                    610                 615                 620
    Asp Ser Ser Tyr Asn Ser Leu Tyr Ser Thr Cys Leu Glu Leu Phe Lys
    625                 630                 635                 640
    Phe Thr Ile Gly Met Gly Asp Leu Glu Phe Thr Glu Asn Tyr Asp Phe
                        645                 650                 655
    Lys Ala Val Phe Ile Ile Leu Leu Ala Tyr Val Ile Leu Thr Tyr
                    660                 665                 670
    Ile Leu Leu Leu Asn Met Leu Ile Ala Leu Met Gly Glu Thr Val Asn
                    675                 680                 685
    Lys Ile Ala Gln Glu Ser Lys Asn Ile Trp Lys Leu Gln Arg Ala Ile
                    690                 695                 700
    Thr Ile Leu Asp Thr Glu Lys Ser Phe Leu Lys Cys Met Arg Lys Ala
    705                 710                 715                 720
    Phe Arg Ser Gly Lys Leu Leu Gln Val Gly Tyr Thr Pro Asp Gly Lys
                        725                 730                 735
    Asp Asp Tyr Arg Trp Cys Phe Arg Val Asp Glu Val Asn Trp Thr Thr
                    740                 745                 750
    Trp Asn Thr Asn Val Gly Ile Ile Asn Glu Asp Pro Gly Asn Cys Glu
                    755                 760                 765
    Gly Val Lys Arg Thr Leu Ser Phe Ser Leu Arg Ser Ser Arg Val Ser
                    770                 775                 780
    Gly Arg His Trp Lys Asn Phe Ala Leu Val Pro Leu Leu Arg Glu Ala
    785                 790                 795                 800
    Ser Ala Arg Asp Arg Gln Ser Ala Gln Pro Glu Glu Val Tyr Leu Arg
                        805                 810                 815
    Gln Phe Ser Gly Ser Leu Lys Pro Glu Asp Ala Glu Val Phe Lys Ser
                    820                 825                 830
```

Pro Ala Ala Ser Gly Glu Lys
            835

<210> SEQ ID NO 5
<211> LENGTH: 511
<212> TYPE: PRT
<213> ORGANISM: Homo sapiens
<220> FEATURE:
<221> NAME/KEY: TRANSMEM
<222> LOCATION: (434)..(455)
<223> OTHER INFORMATION: TM1
<221> NAME/KEY: TRANSMEM
<222> LOCATION: (480)..(495)
<223> OTHER INFORMATION: TM2

<400> SEQUENCE: 5

Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
                 20                  25                  30

Pro Pro Pro Ala Lys Pro Gln Leu Ser Thr Ala Lys Ser Arg Thr Arg
             35                  40                  45

Leu Phe Gly Lys Gly Asp Ser Glu Glu Ala Phe Pro Val Asp Cys Pro
     50                  55                  60

His Glu Glu Gly Glu Leu Asp Ser Cys Pro Thr Ile Thr Val Ser Pro
 65                  70                  75                  80

Val Ile Thr Ile Gln Arg Pro Gly Asp Gly Ser Thr Gly Ala Arg Leu
                 85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Ile Leu Gly Ala Lys Leu
305                 310                 315                 320

-continued

```
His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
        435                 440                 445

Phe Thr Met Ala Ala Tyr Tyr Arg Pro Val Asp Gly Leu Pro Pro Phe
    450                 455                 460

Lys Met Glu Lys Ile Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
                485                 490                 495

Leu Gln Ala Ala Val Asp Glu Asp Pro Val Cys Gly Gln Leu Gln
            500                 505                 510
```

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence:H-FLAG epitope

<400> SEQUENCE: 6

```
Ala Ser Pro Thr Tyr Arg Leu Tyr Ser Ala Ser Pro Ala Ser Pro Ala
1               5                   10                  15

Ser Pro Ala Ser Pro Leu Tyr Ser
            20
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:His6x epitope

<400> SEQUENCE: 7

```
His His His His His His
1               5
```

<210> SEQ ID NO 8
<211> LENGTH: 2633
<212> TYPE: DNA
<213> ORGANISM: Rattus sp.
<300> PUBLICATION INFORMATION:
<301> AUTHORS: Caterina, Michael J.
      Schumacher, Mark A.
      Tominaga, Makoto
      Rosen, Tobias A.
      Levine, Jon D.
      Julius, David
<302> TITLE: The capsaicin receptor: a heat-activated ion channel in
      the pain pathway -continued <303> JOURNAL: Nature
<304> VOLUME: 389
<306> PAGES: 816-824
<307> DATE: 1997

<400> SEQUENCE: 8

| | | | | | |
|---|---|---|---|---|---|
| ctggaaagga | tggaacaacg | ggctagctta | gactcagagg | agtctgagtc | cccaccccaa | 60 |
| gagaactcct | gcctggaccc | tccagacaga | gaccctaact | gcaagccacc | tccagtcaag | 120 |
| ccccacatct | tcactaccag | gagtcgtacc | cggcttttttg | ggaagggtga | ctcggaggag | 180 |
| gcctctcccc | tggactgccc | ttatgaggaa | ggcgggctgg | cttcctgccc | tatcatcact | 240 |
| gtcagctctg | ttctaactat | ccagaggcct | ggggatggac | ctgccagtgt | caggccgtca | 300 |
| tcccaggact | ccgtctccgc | tggtgagaag | cccccgaggc | tctatgatcg | caggagcatc | 360 |
| ttcgatgctg | tggctcagag | taactgccag | gagctggaga | gcctgctgcc | cttcctgcag | 420 |
| aggagcaaga | agcgcctgac | tgacagcgag | ttcaaagacc | cagagacagg | aaagacctgt | 480 |
| ctgctaaaag | ccatgctcaa | tctgcacaat | gggcagaatg | acaccatcgc | tctgctcctg | 540 |
| gacgttgccc | ggaagacaga | cagcctgaag | cagtttgtca | atgccagcta | cacagacagc | 600 |
| tactacaagg | gccagacagc | actgcacatt | gccattgaac | ggcggaacat | gacgctggtg | 660 |
| accctcttgg | tggagaatgg | agcagatgtc | caggctgcgg | ctaacgggga | cttcttcaag | 720 |
| aaaaccaaag | ggaggcctgg | cttctacttt | ggtgagctgc | ccctgtccct | ggctgcgtgc | 780 |
| accaaccagc | tggccattgt | gaagttcctg | ctgcagaact | cctggcagcc | tgcagacatc | 840 |
| agcgcccggg | actcagtggg | caacacggtg | cttcatgccc | tggtggaggt | ggcagataac | 900 |
| acagttgaca | acaccaagtt | cgtgacaagc | atgtacaacg | agatcttgat | cctgggggcc | 960 |
| aaactccacc | ccacgctgaa | gctggaagag | atcaccaaca | ggaaggggct | cacgccactg | 1020 |
| gctctggctg | ctagcagtgg | gaagatcggg | gtcttggcct | acattctcca | gagggagatc | 1080 |
| catgaacccg | agtgccgaca | cctatccagg | aagttcaccg | aatgggccta | tgggccagtg | 1140 |
| cactcctccc | tttatgacct | gtcctgcatt | gacacctgtg | aaaagaactc | ggttctggag | 1200 |
| gtgatcgctt | acagcagcag | tgagacccct | aaccgtcatg | acatgcttct | cgtggaaccc | 1260 |
| ttgaaccgac | tcctacagga | caagtgggac | agatttgtca | agcgcatctt | ctacttcaac | 1320 |
| ttcttcgtct | actgcttgta | tatgatcatc | ttcaccgcgg | ctgcctacta | tcggcctgtg | 1380 |
| gaaggcttgc | cccctataa | gctgaaaaac | accgttgggg | actatttccg | agtcaccgga | 1440 |
| gagatcttgt | ctgtgtcagg | aggagtctac | ttcttcttcc | gagggattca | atatttcctg | 1500 |
| cagaggcgac | catccctcaa | gagtttgttt | gtggacagct | acagtgagat | acttttcttt | 1560 |
| gtacagtcgc | tgttcatgct | ggtgtctgtg | gtactgtact | tcagccaacg | caaggagtat | 1620 |
| gtggcttcca | tggtgttctc | cctggccatg | ggctggacca | acatgctcta | ctatacccga | 1680 |
| ggattccagc | agatgggcat | ctatgctgtc | atgattgaga | agatgatcct | cagagacctg | 1740 |
| tgccggttta | tgttcgtcta | cctcgtgttc | ttgtttggat | tttccacagc | tgtggtgaca | 1800 |
| ctgattgagg | atgggaagaa | taactctctg | cctatggagt | ccacaccaca | aagtgccgg | 1860 |
| gggtctgcct | gcaagccagg | taactcttac | aacagcctgt | attccacatg | tctggagctg | 1920 |
| ttcaagttca | ccatcggcat | gggcgacctg | gagttcactg | agaactacga | cttcaaggct | 1980 |
| gtcttcatca | tcctgttact | ggcctatgtg | attctcacct | acatccttct | gctcaacatg | 2040 |
| ctcattgctc | tcatgggtga | gaccgtcaac | aagattgcac | aagagagcaa | gaacatctgg | 2100 |
| aagctgcaga | gagccatcac | catcctggat | acagagaaga | gcttcctgaa | gtgcatgagg | 2160 |

```
aaggccttcc gctctggcaa gctgctgcag gtggggttca ctcctgacgg caaggatgac    2220
taccggtggt gtttcagggt ggacgaggta aactggacta cctggaacac caatgtgggt    2280
atcatcaacg aggacccagg caactgtgag ggcgtcaagc gcaccctgag cttctccctg    2340
aggtcaggcc gagtttcagg gagaaactgg aagaactttg ccctggttcc ccttctgagg    2400
gatgcaagca ctcgagatag acatgccacc cagcaggaag aagttcaact gaagcattat    2460
acgggatccc ttaagccaga ggatgctgag gttttcaagg attccatggt cccaggggag    2520
aaataatgga cactatgcag ggatcaatgc ggggtctttg ggtggtctgc ttagggaacc    2580
agcagggttg acgttatctg ggtccactct gtgcctgcct aggcacattc cta           2633
```

<210> SEQ ID NO 9
<211> LENGTH: 838
<212> TYPE: PRT
<213> ORGANISM: Rattus sp.
<300> PUBLICATION INFORMATION:
<301> AUTHORS: Caterina, Michael J.
      Schumacher, Mark A.
      Tominaga, Makoto
      Rosen, Tobias A.
<302> TITLE: The capsaicin receptor: a heat-activated ion channel in
      the pain pathway
<303> JOURNAL: Nature
<304> VOLUME: 389
<306> PAGES: 816-824
<307> DATE: 1997

<400> SEQUENCE: 9

```
Met Glu Gln Arg Ala Ser Leu Asp Ser Glu Glu Ser Glu Ser Pro Pro
 1               5                  10                  15

Gln Glu Asn Ser Cys Leu Asp Pro Pro Asp Arg Asp Pro Asn Cys Lys
            20                  25                  30

Pro Pro Pro Val Lys Pro His Ile Phe Thr Thr Arg Ser Arg Thr Arg
        35                  40                  45

Leu Phe Gly Lys Gly Asp Ser Glu Glu Ala Ser Pro Leu Asp Cys Pro
 50                  55                  60

Tyr Glu Glu Gly Gly Leu Ala Ser Cys Pro Ile Ile Thr Val Ser Ser
 65                  70                  75                  80

Val Leu Thr Ile Gln Arg Pro Gly Asp Gly Pro Ala Ser Val Arg Pro
                85                  90                  95

Ser Ser Gln Asp Ser Val Ser Ala Gly Glu Lys Pro Pro Arg Leu Tyr
            100                 105                 110

Asp Arg Arg Ser Ile Phe Asp Ala Val Ala Gln Ser Asn Cys Gln Glu
        115                 120                 125

Leu Glu Ser Leu Leu Pro Phe Leu Gln Arg Ser Lys Lys Arg Leu Thr
130                 135                 140

Asp Ser Glu Phe Lys Asp Pro Glu Thr Gly Lys Thr Cys Leu Leu Lys
145                 150                 155                 160

Ala Met Leu Asn Leu His Asn Gly Gln Asn Asp Thr Ile Ala Leu Leu
                165                 170                 175

Leu Asp Val Ala Arg Lys Thr Asp Ser Leu Lys Gln Phe Val Asn Ala
            180                 185                 190

Ser Tyr Thr Asp Ser Tyr Tyr Lys Gly Gln Thr Ala Leu His Ile Ala
        195                 200                 205

Ile Glu Arg Arg Asn Met Thr Leu Val Thr Leu Leu Val Glu Asn Gly
    210                 215                 220

Ala Asp Val Gln Ala Ala Ala Asn Gly Asp Phe Phe Lys Lys Thr Lys
225                 230                 235                 240
```

-continued

```
Gly Arg Pro Gly Phe Tyr Phe Gly Glu Leu Pro Leu Ser Leu Ala Ala
            245                 250                 255

Cys Thr Asn Gln Leu Ala Ile Val Lys Phe Leu Gln Asn Ser Trp
        260                 265                 270

Gln Pro Ala Asp Ile Ser Ala Arg Asp Ser Val Gly Asn Thr Val Leu
        275                 280                 285

His Ala Leu Val Glu Val Ala Asp Asn Thr Val Asp Asn Thr Lys Phe
290                 295                 300

Val Thr Ser Met Tyr Asn Glu Ile Leu Ile Leu Gly Ala Lys Leu His
305                 310                 315                 320

Pro Thr Leu Lys Leu Glu Glu Ile Thr Asn Arg Lys Gly Leu Thr Pro
                325                 330                 335

Leu Ala Leu Ala Ala Ser Ser Gly Lys Ile Gly Val Leu Ala Tyr Ile
                340                 345                 350

Leu Gln Arg Glu Ile His Glu Pro Glu Cys Arg His Leu Ser Arg Lys
                355                 360                 365

Phe Thr Glu Trp Ala Tyr Gly Pro Val His Ser Ser Leu Tyr Asp Leu
                370                 375                 380

Ser Cys Ile Asp Thr Cys Glu Lys Asn Ser Val Leu Glu Val Ile Ala
385                 390                 395                 400

Tyr Ser Ser Ser Glu Thr Pro Asn Arg His Asp Met Leu Leu Val Glu
                    405                 410                 415

Pro Leu Asn Arg Leu Leu Gln Asp Lys Trp Asp Arg Phe Val Lys Arg
                420                 425                 430

Ile Phe Tyr Phe Asn Phe Phe Val Tyr Cys Leu Tyr Met Ile Ile Phe
                435                 440                 445

Thr Ala Ala Tyr Tyr Arg Pro Val Glu Gly Leu Pro Pro Tyr Lys
                450                 455                 460

Leu Lys Asn Thr Val Gly Asp Tyr Phe Arg Val Thr Gly Glu Ile Leu
465                 470                 475                 480

Ser Val Ser Gly Gly Val Tyr Phe Phe Arg Gly Ile Gln Tyr Phe
                485                 490                 495

Leu Gln Arg Arg Pro Ser Leu Lys Ser Leu Phe Val Asp Ser Tyr Ser
                500                 505                 510

Glu Ile Leu Phe Phe Val Gln Ser Leu Phe Met Leu Val Ser Val Val
                515                 520                 525

Leu Tyr Phe Ser Gln Arg Lys Glu Tyr Val Ala Ser Met Val Phe Ser
                530                 535                 540

Leu Ala Met Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Leu Val Phe Leu Phe Gly Phe Ser
                580                 585                 590

Thr Ala Val Val Thr Leu Ile Glu Asp Gly Lys Asn Asn Ser Leu Pro
                595                 600                 605

Met Glu Ser Thr Pro His Lys Cys Arg Gly Ser Ala Cys Lys Pro Gly
                610                 615                 620

Asn Ser Tyr Asn Ser Leu Tyr Ser Thr Cys Leu Glu Leu Phe Lys Phe
625                 630                 635                 640

Thr Ile Gly Met Gly Asp Leu Glu Phe Thr Glu Asn Tyr Asp Phe Lys
                645                 650                 655
```

```
Ala Val Phe Ile Ile Leu Leu Ala Tyr Val Ile Leu Thr Tyr Ile
            660                 665                 670
Leu Leu Leu Asn Met Leu Ile Ala Leu Met Gly Glu Thr Val Asn Lys
        675                 680                 685
Ile Ala Gln Glu Ser Lys Asn Ile Trp Lys Leu Gln Arg Ala Ile Thr
    690                 695                 700
Ile Leu Asp Thr Glu Lys Ser Phe Leu Cys Met Arg Lys Ala Phe
705                 710                 715                 720
Arg Ser Gly Lys Leu Leu Gln Val Gly Phe Thr Pro Asp Gly Lys Asp
                725                 730                 735
Asp Tyr Arg Trp Cys Phe Arg Val Asp Glu Val Asn Trp Thr Thr Trp
            740                 745                 750
Asn Thr Asn Val Gly Ile Ile Asn Glu Asp Pro Gly Asn Cys Glu Gly
        755                 760                 765
Val Lys Arg Thr Leu Ser Phe Ser Leu Arg Ser Gly Arg Val Ser Gly
    770                 775                 780
Arg Asn Trp Lys Asn Phe Ala Leu Val Pro Leu Leu Arg Asp Ala Ser
785                 790                 795                 800
Thr Arg Asp Arg His Ala Thr Gln Gln Glu Glu Val Gln Leu Lys His
                805                 810                 815
Tyr Thr Gly Ser Leu Lys Pro Glu Asp Ala Glu Val Phe Lys Asp Ser
            820                 825                 830
Met Val Pro Gly Glu Lys
        835

<210> SEQ ID NO 10
<211> LENGTH: 502
<212> TYPE: DNA
<213> ORGANISM: Rattus sp.

<400> SEQUENCE: 10
agatcttgat cctgggggcc aaactccacc ccacgctgaa gctggaagag atcaccaaca      60
ggaagggct cacgccactg gctctggctg ctagcagtgg gaagatcggg gtcttggcct     120
acattctcca gagggagatc catgaaccog agtgccgaca cctatccagg aagttcaccg    180
aatgggccta tggccagtga cactcctccc tttatgacct gtcctgcatt gacacctgtg    240
aaaagaactc ggttctggag gtgatcgctt acagcagcag tgagacccct aaccgtcatg    300
acatgcttct cgtggaaccc ttgaaccgac tcctacagga caagtgggac agatttgtca    360
agcgcatctt ctacttcaac ttcttcgtct actgcttgta tatgatcatc ttcaccgcgg    420
ctgcctacta tcggcctgtg aaggcttgc cccctataa gctgaaaaac accgttgggg    480
actatttccg agtcaccgga ga                                            502

<210> SEQ ID NO 11
<211> LENGTH: 819
<212> TYPE: DNA
<213> ORGANISM: Rattus sp.

<400> SEQUENCE: 11
ccatgggctg gaccaacatg ctctactata cccgaggatt ccagcagatg ggcatctatg      60
ctgtcatgat tgagaagatg atcctcagag acctgtgccg gtttatgttc gtctacctcg    120
tgttcttgtt tggatttttcc acagctgtgg tgacactgat tgaggatggg aagaataact    180
ctctgcctat ggagtccaca ccacacaagt gccggggtc tgcctgcaag ccaggtaact    240
cttacaacag cctgtattcc acatgtctgg agctgttcaa gttcaccatc ggcatgggcg    300
```

```
acctggagtt cactgagaac tacgacttca aggctgtctt catcatcctg ttactggcct    360
atgtgattct cacctacatc cttctgctca acatgctcat tgctctcatg ggtgagaccg    420
tcaacaagat tgcacaagag agcaagaaca tctggaagct gcagagagcc atcaccatcc    480
tggatacaga gaagagcttc ctgaagtgca tgaggaaggc cttccgctct ggcaagctgc    540
tgcaggtggg gttcactcct gacggcaagg atgactaccg gtggtgtttc agggtggacg    600
aggtaaactg gactacctgg aacaccaatg tgggtatcat caacgaggac ccaggcaact    660
gtgagggcgt caagcgcacc ctgagcttct ccctgaggtc aggccgagtt tcaggagaa     720 actggaagaa ctttgccctg gttccccttc tgagggatgc aagcactcga gatagacatg    780
ccacccagca ggaagaagtt caactgaagc attatacgg                           819

<210> SEQ ID NO 12
<211> LENGTH: 20
<212> TYPE: DNA
<213> ORGANISM: Rattus sp.

<400> SEQUENCE: 12
ctggaaagga tggaacaacg                                                20

<210> SEQ ID NO 13
<211> LENGTH: 28
<212> TYPE: DNA
<213> ORGANISM: Rattus sp.

<400> SEQUENCE: 13
gctctagata ggaatgtgcc taggcagg                                       28
```

HUMAN CAPSAICIN RECEPTOR AND USES THEREOF

This application claims benefit of U.S. application Ser. No. 60/155,617, filed Sep. 23, 1999.

BACKGROUND OF THE INVENTION

The sensation of pain can be triggered by any number of physical or chemical stimuli. In mammals, the peripheral terminals of a group of specialized small diameter sensory neurons, termed "nociceptors" mediate this response to a potentially harmful stimulus.

In efforts to discover better analgesics for the treatment of both acute and chronic pain, and to develop treatments for various neuropathic pain states, considerable research has been focused on the molecular mechanism of nociception. The response to heat, low extracellular pH, or capsaicin (the compound responsible for the hotness of hot peppers) is characterized by the persistent activation of nociceptors (Bevan and Gepetti, 1994, and Kress and Reeh, 1996). It has been shown that both heat and capsaicin are capable of activating dorsal root ganglion and trigeminal ganglion neurons via and influx of cations (Oh, et al. 1996, Kirshstein, et al. 1997). Additionally, moderately acidic conditions produce this response (Zeilhofer, et al., 1997) and also potentiate the response of nociceptors to heat and capsaicin (Kress, et al., 1996).

Capsaicin responses in isolated sensory neurons show dose-dependence and are also evoked by structural analogues of capsaicin (Szolcsanyi and Jancso-Gabor, 1975 and 1976). Resiniferatoxin (RTX), a natural product of Euphorbia plants is a particularly potent activator of the capsaicin response (Szallasi and Blumberg, 1989). Capsaicin and resiniferatoxin share a common vanilloid moiety, thus the capsaicin receptor is also termed the vanilloid receptor (VR). The capsaicin response is competitively inhibited by another structural analog, capsazepine (Bevan, et al., 1992) and by the non-selective cation channel blocker ruthenium red (Wood, 1988).

It was initially postulated that the VR is a non-selective cation channel with a preference for calcium. Consequently, a $^{45}Ca^{2+}$-uptake assay using intact rat dorsal root ganglion (DRG) neurons has been used extensively to characterize structure-activity relations for vanilloids. Specific binding of [$^3$H]RTX provided the first unequivocal proof for the existence of a VR and has furnished a new, biochemical tool to study VR pharmacology. Such studies, however, have been limited by the lack of availability of cloned VR species and sub-types, by the low levels of VR produced by the few cell types that naturally express such receptors in vivo, and by the limited expression levels heretofore obtained using transient recombinant expression technologies.

Interest in characterizing VRs led to the cloning of a functional rat capsaicin receptor (VR1), from a rat dorsal root ganglion cDNA library (Caterina, et al., 1997). The cDNA for the rat capsaicin receptor VR1 encodes an 838 amino acid protein (SEQ ID NO:9) with a predicted molecular mass of 95,000 Daltons. Sequence analysis suggests that the receptor is composed of a 432 amino acid hydrophilic amino terminus that contains a proline-rich region followed by three ankyrin repeat domains, a membrane bound region that includes 6 beta-sheet transmembrane domains as well as an additional membrane-associated region between transmembrane segments 5 and 6, and a 154 amino acid carboxy terminus.

VR1 is activated not only by vanilloids but also by noxious heat and low pH. As predicted, this VR1 is a relatively non-selective cation channel with a preference for calcium. In *Xenopus* oocytes expressing VR1, vanilloids evoke inward currents, with RTX being approximately 20-fold more potent ($EC_{50}=39$ nM) than capsaicin ($EC_{50}=710$ nM). In VR1-transfected mammalian (HEK293) cells, capsaicin induces whole-cell currents with a potency of 110 nM. Taken together, these results suggest that VR1 corresponds to the site in DRG neurons that mediates calcium uptake.

Homology searches comparing the cloned rat capsaicin receptor VR1 to other known ligand gated channels have revealed some related receptors. The most highly homologous protein identified to date is the recently identified rat vanilloid-receptor-like protein 1 (VRL-1) (Caterina, et al. 1999). This protein shares approximately 49% identical amino acid residues and overall is 66% similar in sequence to the rat capsaicin receptor, VR1, and is predicted to have a tertiary structure quite similar to that of the capsaicin receptor. While the VRL-1 protein has been reported to respond to high temperatures by allowing an influx of cations, it is not a capsaicin receptor, as it is insensitive to capsaicin and capsaicin analogues.

Another class of receptors that shows some homology to the capsaicin receptor is the TRP (transient release potential) family of putative store-operated calcium channels. (Caterina, et al., 1997) also known as "trp channels". Members of this family of receptors mediate the entry of extracellular $Ca^{2+}$ in response to the depletion of intracellular $Ca^{2+}$ stores (Clapham, 1996). The capsaicin receptor, while mediating the entry of $Ca^{2+}$ and other cations in response to heat, low extracellular pH and capsaicin and related compounds, does not act as a store-operated calcium channel.

If vanilloid binding and calcium uptake are always mediated by the same receptor, a logical prediction would be that ligands mediating these two responses should display similar structure-activity relationships. With regard to DRG neurons expressing native VRs this is clearly not the case: structure-activity analysis of different vanilloid derivatives revealed that the various compounds have distinct potencies for receptor binding and for inducing $^{45}Ca^{2+}$-uptake in rat DRG neurons. Although some compounds, such as RTX-amide, bind to VRs and evoke calcium influx with similar potencies, other vanilloids show relative selectivity for one or the other response. RTX represents one extreme. It is approximately 25-fold more potent for binding (using intact rat DRG neurons the $K_d$ was reported to be 40 pM) than for inducing calcium uptake ($EC_{50}=1.0$ nM). Capsaicin represents the opposite extreme. It evokes calcium influx with an $EC_{50}$ of 270 nM but inhibits [$^3$H]RTX binding with a 10-fold lower affinity of 3 uM. The most straightforward explanation appeared to be that RTX binding and calcium uptake detected two distinct classes of VRs. These putative receptors were referred to as R-type (preferentially labeled by RTX) and C-type (displaying a higher potency for capsaicin) VRs, respectively. This model was further supported by the identification of non-neuronal cell lines that exhibited calcium uptake in response to vanilloid stimulation (implying the presence of C-type VRs) but which lacked detectable RTX-specific binding sites.

BRIEF DESCRIPTION OF THE DRAWINGS

In FIG. 4A and FIG. 4b, traces from a representative side-by-side comparison of capsaicin and resiniferatoxin effects are displayed. Note that these two typical vanilloid agonists display substantially different kinetics from the responses they evoke.

FIG. 4B. Time dependence of resiniferatoxin-evoked calcium mobilization in CHO/VR1 cells in response to 0.01 nM, 1 M and 100 nM resiniferatoxin.

DESCRIPTION OF THE SEQUENCE LISTINGS

Figure 1A:
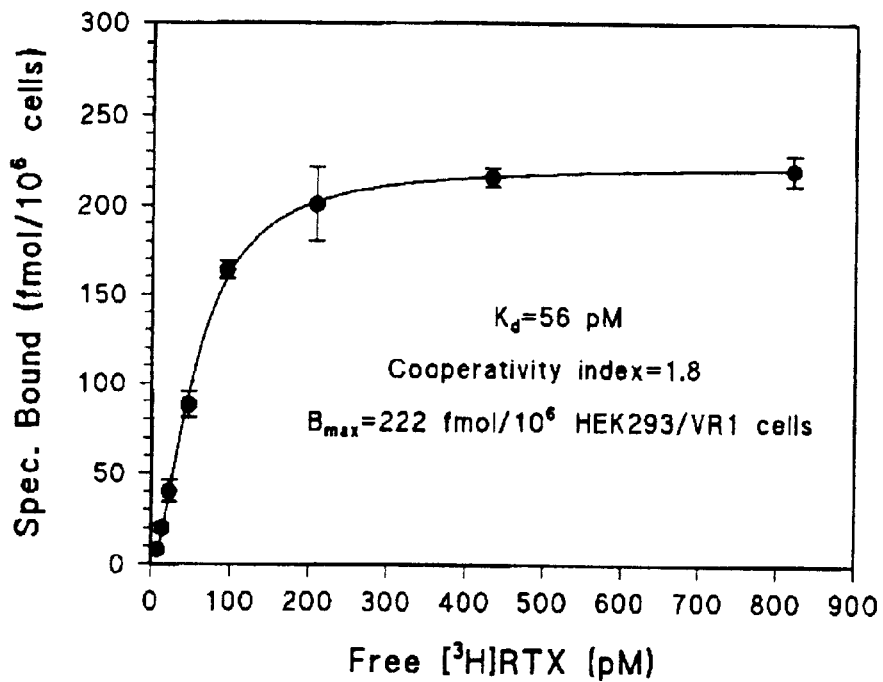
FIG. 1A. Specific binding of [$^3$H]resiniferatoxin to HEK 293 cells transfected stably with a cDNA encoding the rat VR1 (HEK293/VR1 cells). [$^3$H]Resiniferatoxin displays saturable specific binding to HEK293/VR1 cells. Binding data are from a single experiment; points are mean values of triplicate determinations; error bars indicate S.E.M. The binding curve was generated by a computer fit of the measured values to the Hill equation. Half-maximal binding occurred at a concentration of 56 pM [$^3$H]resiniferatoxin; the maximal receptor density was 222 fmol per one million cells. Note that the Hill coefficient (1.8) is indicative of positive binding cooperativity. Three additional experiments yielded similar results. Data are presented as the mean (+/−S.E.M), and binding parameters are set forth in Example 6, Results.

SEQ ID NO:1. Human capsaicin receptor cDNA.

SEQ ID NO:2. Human capsaicin receptor cDNA. Differs from SEQ ID NO:1 only in the 5' and 3' untranslated regions.

SEQ ID NO:3. DNA encoding Short form of Human capsaicin receptor.

SEQ ID NO:4. Protein encoded by both SEQ ID NO:1 and SEQ ID NO:2. Transmembrane domains span residues thusly: TM1=434–455, TM2=480–495, TM3=510–530, TM4=543–569, TM5=577–596, TM6=656–684.

SEQ ID NO:5. Protein encoded by SEQ ID NO:3. Transmembrane domains span residues thusly: TM1=434–455, TM2=480–495.

SEQ ID NO:6. Amino acid sequence of FLAG epitope.

SEQ ID NO:7. Amino acid sequence of His6x epitope.

SEQ ID NO:8. Rat capsaicin receptor VR1 cDNA sequence.

SEQ ID NO:9. Rat capsaicin receptor VR1 amino acid sequence.

SEQ ID NO:10. The DNA sequence of a 500 bp Bgl II fragment of the rat VR1 cDNA (used as a probe).

SEQ ID NO:11. The DNA sequence of an 830 bp BamHI/NcoI fragment of the rat VR1 cDNA (used as a probe).

SEQ ID NO:12. Forward primer used to clone rat VR1 cDNA.

SEQ ID NO:13. Reverse primer used to clone rat VR1 cDNA.

SUMMARY OF THE INVENTION

This invention relates to novel human capsaicin receptor polypeptides and the nucleotide sequences encoding them. Also included in this invention are nucleic acid vectors (e.g., plasmids) comprising the nucleotide sequence encoding these receptors, mammalian and non-mammalian cell lines comprising such vectors and thereby expressing at least one of the receptor polypeptides, and purified membranes obtained from such mammalian and non-mammalian cell lines. In certain preferred embodiments the polypeptides are full-length active human capsaicin receptor proteins that are capable of binding to capsaicin or capsaicin analogues. In other embodiments the receptors are naturally occurring truncated human capsaicin receptor proteins that are expressed at higher levels in bacterial cells than are full-length human capsaicin receptor proteins. Such truncated proteins are useful for bacterial expression e.g., for the production of immunogens for use in preparing anti-capsaicin receptor antibodies.

In another aspect, this invention relates to assays for identifying compounds that modulate capsaicin receptors, such assays requiring recombinantly expressed active human capsaicin receptor proteins that are capable of binding to capsaicin or capsaicin analogues. Cell lines that express the human capsaicin receptor are useful for screening compounds for either agonist, reverse agonist or antagonist activity at capsaicin receptors. Compounds that act as agonists at the human capsaicin receptor are useful as flavoring agents or animal repellents, while those that act as antagonists or reverse agonists may be useful as analgesics or anesthetics.

In a separate aspect this invention relates to diagnostic assays for capsaicin receptor polymorphisms and aberrant capsaicin receptor expression levels. Such assays are useful for identifying individuals that are either particularly susceptible or particularly insusceptible to the types of pain mediated by the capsaicin receptor and thereby for determining which individuals will benefit from and which will prove refractory to treatment with modulators of this receptor.

DETAILED DESCRIPTION OF THE INVENTION

Nucleic Acids

The present invention provides isolated nucleic acid molecules encoding human capsaicin receptors. Isolated nucleic acid molecules encoding human capsaicin receptors comprise DNA molecules, such as genomic DNA molecules, cDNA molecules, or RNA molecules. In one embodiment the isolated nucleic acid molecule is the cDNA sequence shown SEQ ID NO:1. In a separate embodiment the isolated nucleic acid molecule is the cDNA sequence shown is SEQ ID NO:2. In another embodiment the isolated nucleic acid molecule is the cDNA sequence shown in SEQ ID NO:3. SEQ ID NO:1 and SEQ ID NO:2 differ in their non-coding regions, while SEQ ID NO:3 encodes a shortened (truncated) form of the human capsaicin receptor, as well as containing a different 5' non-coding region.

The invention also includes an isolated nucleic acid molecule encoding the amino acid sequence of SEQ ID NO:4 and an isolated nucleic acid molecule encoding the amino acid sequence of SEQ ID NO:5, in certain preferred embodiments the nucleic acid molecules encode polypeptides with amino acid sequences corresponding to the sequences starting with amino acid 2 (Lys) of SEQ ID NO:4 or SEQ ID NO:5. Also included is an isolated nucleic acid molecule encoding a human capsaicin receptor sequence comprising the amino acid sequence consisting essentially of SEQ ID NO:5.

It will be apparent to those skilled in the art that due to the degeneracy of the genetic code numerous variants of the described nucleic acid molecules can be created by substituting 1 or more codons without changing the encoded amino acid sequence of the protein product. Additionally, nucleic acid changes may be made in the non-coding region of the nucleic acid sequences without altering the amino acid sequence of the protein product.

The present invention also encompasses DNA and cDNA sequences that encode amino acid sequences which differ from those of the human capsaicin receptor but which do not produce phenotypic changes. Preferably such changes are conservative amino acid changes. By the term "conservative amino acid change" is meant any change from one amino acid to another amino acid considered to have similar characteristics (see, e.g., Schulz & Schirmer, 1990) as set forth in Table I hereto.

TABLE I

Amino Acids Grouped by Characteristics

| Basic Side Chains | Acidic Side Chains | Large Aliphatic Side Chains | Aromatic Side Chains | Polar Side Chains |
| --- | --- | --- | --- | --- |
| Lysine, Arginine, Histidine | Aspartate, Glutamate | Leucine, Isoleucine, Valine, Cysteine, Methionine | Phenylalanine, Tyrosine, Tryptophan | Glycine, Alanine, Proline, Serine, Threonine, Asparagine, Glutamine |

Also within the scope of the present invention are other changes to DNA and cDNA sequences encoding the amino acid sequences of SEQ ID NO:4 and SEQ ID NO:5 are in-frame additions of nucleic acid sequences encoding useful amino acid sequence tags. Such tags are useful as, e.g., antibody recognition sites and as sites contributing strong binding interaction characteristics (such as glutathione-S-transferase binding, biotin binding, or metal chelation binding) that are useful for facilitating protein purification via, e.g. affinity chromatography. Such amino acid sequences are well known in the art, and include, but are not limited to the His-6x epitope (SEQ ID NO:6), which chelates copper and other metal ions and is specifically bound by the Monoclonal Anti-polyhistidine Clone HIS-1 monoclonal antibody (Sigma, St. Louis No. H1029), and the FLAG epitope (SEQ ID NO:7), which is specifically bound by the FLAG-M2 monoclonal antibody (Sigma, St. Louis No. F3165). Techniques for making such modifications are also well known in the art, and may be readily carried out using routine methods or by using commercially available kits, for example, the Sigma Mammalian FLAG Expression Kits (Sigma, St. Louis, e.g., Nos. FL-MA and FL-MC).

Also included in the invention are DNA and cDNA sequences encoding human capsaicin receptors identical to those of SEQ ID NO:4 or SEQ ID NO:5, except in the regions encoding their transmembrane domains (as set forth below in the SEQUENCE LISTING). The transmembrane domains of the capsaicin receptor are believed to be β strands. Sequences consisting essentially of the amino acids Tyrosine, Tryptophan, Valine, Threonine, Glutamine, Methionine, Leucine, Isoleucine, Phenylalanine and Cysteine are known to have high propensities for forming β strands (Chou and Fasman, 1974). Substitution of nucleotides encoding any of these amino acids for nucleotides encoding other amino acids in the transmembrane regions of the capsaicin receptors of SEQ ID NO:4 and SEQ ID NO:5 will result in functional receptor translation products, and are within the scope of the present invention.

Polypeptides

This invention provides isolated human capsaicin receptor polypeptides having the amino acid sequence of SEQ ID NO:4 or SEQ ID NO:5. In certain preferred embodiments the polypeptides have amino acid sequences corresponding to the sequences starting with amino acid 2 (Lys) of SEQ ID NO:4 or SEQ ID NO:5. The amino acid sequence given by SEQ ID NO:4 is the protein product encoded by both SEQ ID NO:1 and SEQ ID NO:2. The amino acid sequence given by SEQ ID NO:5 is the protein product encoded by SEQ ID NO:3.

This invention also encompasses human capsaicin receptors having amino acid sequences that further differ from those exemplified herein, but which do not exhibit phenotypic changes. Such amino acid sequences are described above in the discussion of nucleotide sequences, and further include human capsaicin receptors having amino acid sequences that differ from those of SEQ ID NO:4 and SEQ ID NO:5 in the transmembrane domains of the protein without eliminating capsaicin receptor binding or signaling functions. The regions of the amino acid sequences for the receptor considered to represent the transmembrane domains of the protein are annotated as TM1, TM2, TM3, TM4, TM5 and TM6 in the sequence listing for SEQ ID NO:4 and SEQ ID NO:5. It is predicted that the transmembrane domains of the capsaicin receptor are β strands. The amino acids Tyrosine, Tryptophan, Valine, Threonine, Glutamine, Methionine, Leucine, Isoleucine, Phenylalanine and Cysteine are known to have high propensities for being in β strands (Chou and Fasman, 1974). Amino acid sequences of the human capsaicin receptor having of any of these amino acids substituted for other amino acids in the transmembrane domains are encompassed by this invention.

Vectors Encoding the Human Capsaicin Receptor

The present invention additionally provides nucleic acid vectors comprising a nucleic acid sequence encoding a polypeptide with the amino acid sequence of SEQ ID NO:4 or SEQ ID NO:5 or, in certain preferred embodiments, encoding amino acid sequences corresponding to the sequences starting with amino acid 2 (Lys) of SEQ ID NO:4 or SEQ ID NO:5. Such nucleic acid sequences include any of the above-described nucleic acid a sequences. Suitable vectors include, but are not limited to, a plasmid or a viral vectors. In order for the vector to be used for recombinant expression of a capsaicin receptor, the nucleic acid sequence encoding the receptor must be operatively linked to a nucleic acid sequence comprising at least one regulatory element in the appropriate orientation for expression. Such regulatory elements are well known to those of skill in the art. Preferred regulatory elements are heterologous regulatory elements, i.e., regulatory elements that are not naturally found operatively linked to nucleic acid sequences encoding human capsaicin receptor polypeptides. Such elements include those obtained from other mammalian species as well as those from non-mammalian vertebrates, invertebrates, microbes and viruses. Particualrly preferred regulatory elements are inducible elements, i.e., elements that do not always stimulate expression (or only stimulate relatively low levels of expression), but that respond to environmental stimuli by increasing expression levels of the operatively linked coding sequences. A preferred inducible element is the tetracycline repressible element found in the commercially available pTET OFF™ plasmid vector.

Propagation of the vectors of the invention in microbial hosts is facilitated by the presence in the vector of sequences that act as origins of replication for microbial DNA synthesis, but such microbial-specific sequences are considered to reduce the rate of success in generating certain recombinant cells (particularly in generating transgenic animals), and thus such microbial sequences may be beneficially excised (e.g., by restriction enzyme digestion) prior to the introduction of the vector into an animal cell (e.g., a vertebrate zygote).

The vectors of the invention may be transformed, transfected, microinjected, or otherwise introduced into suitable host cells to form host cell-vector systems for the expression of a polypeptide of the invention. In certain preferred embodiments, the polypeptide exhibits human capsaicin receptor binding and/or signaling activity.

This invention encompasses any of the above-described vectors adapted for infection or transformation of a bacterial cell. Bacterial expression systems for the expression of membrane receptor proteins are available (Muench, et al. 1995). Bacterial host vector systems are also useful in that (when the appropriate microbial origin of DNA replication is present in the vector) they allow the production of large quantities of DNA or (when an appropriate microbial RNA polymerase transcription initiation site is present in the appropriate orientation for RNA expression) of RNA encoding the polypeptides of the invention. A particularly preferred vector for the bacterial expression of the polypeptides of SEQ ID NO:5 is the be pRSET vector that is commercially available from Invitrogen (Carlsbad, Calif.). Protein expression using this vector can be conveniently induced by adding the lactose analog isopropylthiogalactoside (IPTG) to the bacterial culture medium.

This invention also encompasses the above-described vector adapted for expression in a eucaryotic cell (preferably an insect cell, an amphibian cell, or a mammalian cell) which vector further comprises heterologous regulatory elements allowing expression in the cell operatively linked to a nucleic acid molecule encoding at least one polypeptide of the invention, so as to permit expression thereof.

In one embodiment, the vector is adapted for expression in an insect cell. Plasmids commonly used to generate such vectors for this purpose include the BacPak8 and BacPak9 baculoviral vector plasmids (Clontech, Palo Alto, Calif.). These plasmid vectors typically include a multiple cloning site for the insertion in the appropriate orientation for expression of a DNA fragment comprising the sequence encoding the polypeptide to be expressed, such as any of the cDNA sequences of SEQ ID NO:1, SEQ ID NO:2, or SEQ ID NO:3, a promoter sequence, a bacterial origin of DNA replication, and markers for antibiotic resistance.

This invention also encompasses the above-described vector adapted for expression in an amphibian cell, preferably a Xenopus laevis oocyte. Plasmids that may be used to generate such vectors for this purpose include the pcDNA3.1 vector (Invitrogen, Carlsbad, Calif.)

In a preferred embodiment, the vector is adapted for expression in a mammalian cell. An example of a plasmid commonly used to generate such vectors for expression of polypeptides (e.g., those of the present invention) in mammalian cells is pBK-CMV (Stratagene, La Jolla, Calif.) in which the regulatory elements include the cytomegalovirus promoter, which is activated by proteins that are ubiquitously expressed in vertebrate cells.

This invention provides plasmid vectors designated PT35, PT36, and PT44, which comprise the regulatory elements necessary for expression of DNA in a mammalian cell operatively linked to the DNA encoding human capsaicin receptor polypeptides of the invention in the appropriate orientation so as to permit expression.

These plasmids, PT35, PT36, and PT44 were deposited on Aug. 27, 1999 with the American Type Culture Collection (ATCC) 10801 University Blvd., Manassas, Va. 20110-2209, U.S.A. under the provisions of the Budapest Treaty for the International Recognition of the Deposit of Microorganisms for the Purposes of Patent Procedure and were accorded Patent Deposit Numbers PTA-576, PTA-577 and PTA-578, respectively. In accordance with 37 CFR 1.808 (a)(2), et seq., all restrictions imposed by the depositor on the availability to the public of the deposited materials will be irrevocably removed upon the granting of a U.S. patent from the present application.

Recombinant Cells Expressing the Human Capsaicin Receptor

In another aspect this invention provides a recombinant cell expressing the human capsaicin receptor polypeptides, said cell having been obtained by adding the above-described vectors to a host cell. Such host cells include cells from cell lines, cells from primary cultures, and ova and oocytes. A preferred cell of this type is a Xenopus laevis oocyte recombinantly expressing active human capsaicin receptor proteins of the invention. Other preferred recombinant cells of the invention include other amphibian cells, insect cells, or mammalian cells comprising at least one of the above-described vectors of the invention. The present invention thus includes such cells comprising such vectors comprising at least the coding regions of the nucleic acid sequences of at least one of SEQ ID NO:1, SEQ ID NO:2, or SEQ ID NO:3, operatively linked to regulatory sequences in the appropriate orientation for the expression of the encoded polypeptides of the invention.

The vector may be added to the host cell by any of the means commonly practiced by those skilled in the art, including but not limited to infection, transformation, transfection or microinjection. Resulting recombinant cells (typically the progeny of the vector-containing host cell) will preferably express at least 2-fold greater capsaicin or capsaicin agonist binding activity (measured, e.g., as described for vanilloid binding in Example 6 hereto), or more preferably at least 10-fold greater binding activity, or most preferably at least 20-fold greater binding activity than a control host cell to which vector has not been added.

In one embodiment the recombinant cell is an insect cell comprising the above-described plasmid or vector. One commonly used insect cell protein expression system is that of *Spodoptera frugiperda* cells infected with a baculovirus vector.

The invention further provides a mammalian cell comprising the above-described vector. Both adherent and non-adherent mammalian cell are appropriate for expression of the human capsaicin receptor polypeptides of the invention. The mammalian cell may be a COS-7 cell, CHO cell, human embryonic kidney 293 cell (HEK 293), a U937 cell or any other suitable mammalian cell, including cells in primary cell cultures. The mammalian cell may also be prepared by generating a transgenic animal (preferably the animal is a rodent or a domestic livestock species such as a pig, cow, got, sheep, rabbit, or chicken). Methods for generating such transgenic animals are well known, and while often of low efficiency and technically demanding, are nonetheless routine in the art.

Artificially high expression levels of ion channels typically have toxic effects on cultured cells. Without wishing to be bound by any particular theory of operation, it is believed that when it occurs, such toxicity results from excess entry of ions (e.g., $Ca^{2+}$) into cells expressing artificially high levels of ion channels. The capsaicin receptors of the invention act as ion channels, and their expression at artificially high levels would thus be expected to be limited by such toxicity.

The present invention provides for recombinant mammalian cells (e.g., cells comprising an expression vector) expressing high levels of capsaicin receptors, or capable of expressing high levels of capsaicin receptors (e.g., upon derepression—for example removal of tetracycline from the growth medium of cells comprising expression vectors of the invention using the regulatory elements of the commercial pTET OFF™ inducible plasmid vector). Such cells express higher numbers of capsaicin binding sites than do naturally occurring cells, and are particularly useful for the preparation of membranes containing capsaicin receptors for use in binding assays for the identification of compounds that interact (preferably ones that specifically interact, e.g., by binding to the ligand-binding site of the receptor) with such receptors. Preferably, the recombinant cells of the invention are stably transfected cells.

Preferred cells express at least $5 \times 10^4$ capsaicin receptor ligand binding sites per cell. Preferably the cells express at least $1.5 \times 10^5$ such binding sites per cell. More preferably the cells express at least $3 \times 10^5$, and even more preferably, $3 \times 10^6$ such binding sites per cell. Most preferably, the cells express at least $10^7$ capsaicin receptor ligand binding sites per cell.

Preferred cells express at least 80 fmol of capsaicin receptor molecules per $10^6$ cells. Preferably the cells express at least 250 fmol of capsaicin receptor molecules per $10^6$ cells. More preferably the cells express at least 470 fmol of capsaicin receptor molecules per $10^6$ cells and even more preferably at least 2 pmol of capsaicin receptor molecules per $10^6$ cells. Most preferably, the cells express at least 16 pmol of capsaicin receptor molecules per $10^6$ cells.

isolated Membranes of Recombinant Cells

In certain of its aspects the present invention provides preparations comprising isolated membranes of the recombinant cells of the invention. Preferably, the isolated membranes should exhibit capsaicin receptor ligand binding activity that is significantly greater, preferably at least 2-fold greater, more preferably at least 10-fold greater and most preferably at least 20-fold greater than that exhibited by control membranes isolated from a control host cell (e.g., a cell of the same cell line used to prepare the recombinant cell of the invention that does not contain any vector, or contains a control vector that does not encode a capsaicin receptor). Preferred membranes contain, per mg of total membrane protein, at least 415 fmol, preferably at least 1.25 pmol, even more preferably 2.35 pmol, particularly preferably 4.2 pmol, and most preferably at least 25 pmol of capsaicin receptor. Membranes can be isolated by any suitable method, such as any of the membrane preparation methods that are routinely used in the art.

Assays for Identifying Modulators of Capsaicin Receptors

In a final aspect, the invention provides methods for determining whether a compound can specifically bind to a capsaicin receptor and methods for determining whether a compound can modulate a capsaicin receptor as either an agonist or an antagonist. Agonist compounds are useful as analgesics. This counter-intuitive result is believed to follow from prolonged receptor desensitization that can occur following exposure to such compounds. Agonists, antagonists and reverse agonists are all useful as analgesics, as well as for the prevention and treatment of other conditions, such as treatment of urinary incontinence, prevention of urinary bladder hyper-reflexia and treatment of certain neuropathic pain states such as post herpetic neuralgia, diabetic neuropathy, carpal tunnel syndrome and phantom limb pain in amputees.

The invention thus provides assays for identifying compounds useful a) as analgesics, b) for the treatment of urinary incontinence, c) for the prevention of urinary bladder hyper-reflexia and d) for the treatment of neuropathic pain states (e.g., post herpetic neuralgia, diabetic neuropathy, carpal tunnel syndrome or phantom limb pain).

The invention in particular provides an assay for determining if a compound binds specifically to capsaicin receptors. This assay comprises contacting an experimental sample of either recombinant cells of the invention or isolated membrane preparation of such cells with a labeled capsaicin agonist and a test compound. A second control sample of either recombinant cells expressing the human capsaicin receptor or an isolated membrane preparation of such cells is contacted only with labeled capsaicin agonist. The unbound labeled agonist is removed from both samples and the amount of bound label in both the experimental sample and the control sample is determined. The amount of bound label in the experimental sample is compared to the amount bound label in the control sample. If the experimental sample exhibits a 2-fold decrease, or more preferably a 5-fold decrease or most preferably a 10-fold decrease in the amount of bound labeled capsaicin agonist the compound in the experimental sample is identified as binding specifically to capsaicin receptors.

In the above-described binding assay the labeled capsaicin agonist may be any agonist that is known to bind specifically to capsaicin receptors, such as capsaicin or resiniferatoxin and may be labeled by any detectable label. Detectable labels include, but are not limited to, radiolabels, fluorescent labels and colorometric labels. A particularly preferred labeled capsaicin agonist is [$^3$H] resiniferatoxin. Removal of unbound label may be accomplished by filtering or washing the samples but is not limited to these methods.

The invention also provides functional assays for identifying compounds that act as modulators of capsaicin receptors. Such assays can be used to classify compounds as agonists or antagonists of the capsaicin receptor.

This invention provides a method for determining whether a compound is a human capsaicin receptor agonist, which comprises contacting a recombinant cell of the invention with the compound under conditions that permit activation of a functional human capsaicin receptor response, detecting a functional increase in human capsaicin receptor activity, and there by determining whether the compound is a human capsaicin receptor agonist.

In one such embodiment the invention provides an assay for determining if a compound is an agonist of capsaicin receptors where the functional response is a change in the concentration of intracellular $Ca^{2+}$. This assay comprises contacting a sample of recombinant cells expressing the human capsaicin receptor with an indicator of intracellular $Ca^{2+}$ concentration to yield indicator-loaded cells. After a sufficient incubation period excess indicator is removed from the cells to yield washed, indicator-loaded cells. A potential agonist compound is added to a sample of the washed, indicator-loaded cells. This sample is the experimental sample; the control sample is comprised of washed, indicator-loaded cells to which no potential agonist compound had been added. The concentrations of intracellular $Ca^{2+}$ experimental and control samples are measured by quantitating a change in the indicator of intracellular $Ca^{2+}$. The concentration of intracellular $Ca^{2+}$ in the experimental cells that have been contacted with a potential agonist compound is compared to the concentration of intracellular $Ca^{2+}$ in the control cells. If the experimental sample exhibits a 1.5-fold increase, or more preferably a 5-fold increase or most preferably a 10-fold increase (or any significant increase) in the concentration of intracellular $Ca^{2+}$ the compound in the experimental sample is identified as a capsaicin receptor agonist. As used herein and in the Claims, a significant change (e.g., increse or decrese) is one that is significant to the $p \leq 0.05$ level in any standard parametric test of statistical significance, such as the F-test, or the Student's T-test.

Particularly preferred indicators of intracellular $Ca^{2+}$ concentration are membrane permeable calcium sensitive dyes, e.g., Fluo-3 and Fura-2. These dyes produce a fluorescent signal when bound to $Ca^{2+}$. Removal of excess indicator from the indicator-loaded cells may be accomplished by washing or filtering cells, but is not limited to these methods.

This invention provides a method for determining whether a compound is a human capsaicin receptor antagonist, which comprises contacting a cell of the invention with the compound in the presence of a known capsaicin receptor agonist, such as capsaicin or resiniferatoxin, under conditions that permit the activation of a functional capsaicin receptor response, detecting a decrease in human capsaicin receptor activity, and thereby determining whether the compound is a human capsaicin receptor antagonist.

In one embodiment, the assay to identify compounds that act as antagonists of capsaicin receptors comprises contacting a test sample of recombinant cells expressing the human capsaicin receptor with an indicator of intracellular $Ca^{2+}$ concentration and a test compound (prefereably the cells are pre-loaded with the indicator). A second control sample of recombinant cells expressing the human capsaicin receptor is contacted only with the indicator of intracellular $Ca^{2+}$ concentration. After a sufficient incubation period excess indicator of intracellular $Ca^{2+}$ is removed from the test and control cells to yield washed, indicator-loaded test and control cells. An agonist of the capsaicin receptor is added to the washed, indicator-loaded cells to yield agonist-contacted test cells and agonist-contacted control cells. The concentration of intracellular $Ca^{2+}$ in the agonist-contacted test cells and the agonist-contacted control cells is measured by measuring changes in the properties of the indicator of intracellular $Ca^{2+}$ concentration. The concentration of intracellular $Ca^{2+}$ in the agonist-contacted test cells is compared to that in agonist-contacted control cells. A test compound for which this comparison indicates that the concentration of intracellular $Ca^{2+}$ in the agonist-contacted test cells is significantly less, to the $p \leq 0.05$ level, than the concentration of intracellular $Ca^{2+}$ in the agonist-contacted control cells is identified as an antagonist of capsaicin receptors.

As in the assay for agonists of the capsaicin receptor, particularly preferred indicators of intracellular $Ca^{2+}$ concentration are the membrane permeable calcium sensitive dyes, Fluo-3 and Fura-2. These dyes produce a fluorescent signal when bound to $Ca^{2+}$. Removal of excess indicator from the indicator-loaded cells may be accomplished by any suitable method, such as washing or filtering cells.

The invention will now be further described with reference to the following examples.

EXAMPLES

Example 1

Isolation of Human Capsaicin Receptor DNA Clones

Poly A+ RNA was isolated from frozen human dorsal root ganglia. A complementary DNA (cDNA) library was constructed using the ZAP EXPRESS cDNA SYNTHESIS KIT and the ZAP EXPRESS cDNA GIGAPAK III GOLD CLONING KIT (Stratagene, La Jolla, Calif.) according to the manufacturer's instructions. This library contained approximately $1.1 \times 10^6$ independent clones. $1 \times 10^6$ plaque forming units (PFU) from this library were plated and transferred to nitrocellulose filters for hybridization screening. Two $^{32}$P labeled probes were used for screening the filters. One probe, SEQ ID NO:10, corresponded to a 500 bp Bgl II fragment of the published rat Vanilloid Receptor 1 cDNA (VR1; Caterina, et al. 1997). The second probe, SEQ ID NO:11, corresponded to an 830 bp BamHI/Nco I fragment of VR1. Filters were hybridized with either probe overnight at 42° C. and subsequently washed at 55° C. in 0.2×SSC/0.1% SDS. Positive phage were isolated and re-screened to obtain a single (clonal) phage. The pBK-CMV phagemid was excised from the clonal lambda phage by using the EXASSIST Helper phage (Stratagene). The resulting plasmids were transformed into *E. coli* strain XLOLR (Stratagene). Plasmid DNA was isolated by maxi prep for sequencing. The nucleotide sequences of the EcoRI/XhoI inserts of the phagemid clones were determined with an ABI CYCLE SEQUENCING KIT (Perkin-Elmer Applied Biosystems, Foster City, Calif.).

Example 2

Recombinant Cells

A. Transiently Transfected Cells

Plasmids PT35, PT36 and PT44 were isolated from XLOLR *E. coli* and separately transfected into HEK 293T cells (Edge Biosystems, Gaithersville, Md.) by adding 2 μg plasmid DNA and 12 μl LIPOFECTAMINE Reagent (Life Technologies cat no. 10964-013, Life Technologies, Gaithersville, Md.) per 60 mm culture plate according to the manufacturer's instructions. Cells were grown for 24 hrs at 37° C. then reseeded onto 96-well plates suitable for use in the FLIPR™ Plate Reader (Molecular Devices, Sunnyvale Calif.). Cells were grown an additional 24–48 hours before assay.

Transfected cells were assayed for changes in detectible $Ca^{2+}$ levels using the Calcium mobilization assay described below in Example 5. The results of these experiments are set forth in Table II.

B. Stably Transfected Cells

Cells stably expressing the human capsaicin receptor are selected using the Neomycin resistance marker present in the PT35, PT36 and PT44 plasmids. HEK 293T cells transiently transfected with the PT35, PT36 or PT44 plasmids as described above are grown in media containing the antibiotic G418 for two weeks to isolate cell lines stably expressing the recombinantly expressed human capsaicin receptor.

C. Inducible Stably Transfected Cells

The cDNA encoding SEQ ID NO:4 is subcloned into the pTRE vector (Clontech, Palo Alto, Calif.) for recombinant expression in mammalian cells. Plasmids are transfected with LIPOFECTAMINE™ into Chinese Hamster Ovary (CHO) cells containing the pTET OFF™ Regulator plasmid (Clontech, Palo Alto, Calif.). In these cells, expression of the pTRE plasmid is repressed in the presence of tetracycline but is induced upon removal of the antibiotic. Stable clones are isolated in culture medium containing puromycin (10 μg/ml) and maintained in medium supplemented with tetracycline (1 μg/ml). Cells are grown without antibiotic for 48–72 hours prior to assay to facilitate maximal expression of the human capsaicin receptor.

Example 3

Purified Membranes of Cells Expressing the Human Capsaicin Receptor

The human capsaicin receptor-transfected HEK 293T cells of Example 2 were seeded into 96 well plates and grown to 70–90% confluency. Cells were harvested by centrifugation at 3500×g and washed once by resuspension in ice cold PBS containing protease inhibitors. Cells were lysed by POLYTRON (speed 5, 30 seconds) and centrifuged at 536×g for 10 minutes in order to remove DNA, cellular organelles, and unlysed cells. The supernatant, containing isolated membranes, was decanted to a clean centrifuge tube and centrifuged for 20 minutes at 40,000×g. The resulting pellet was washed twice in ice cold PBS and centrifuged again for 20 minutes at 40,000×g. The supernatant of this step was discarded. The protein concentration of the resulting membrane pellet was measured using the Bio-Rad (Bradford) protein assay. By this measure, a 1 liter culture of cells typically yielded 50–75 mg of total membrane protein.

Example 4

Radioligand Binding Assay for Modulators of Capsaicin Receptors

Binding studies with [$^3$H] resiniferatoxin (RTX) (NEN, Boston) were carried out according to the protocol of Szallasi, et. al (1992) in which non-specific RTX Binding is reduced by adding bovine $α_1$-glycoprotein (100 μg per tube) after the binding reaction has been terminated. Binding assay mixtures were set up on ice and contained [$^3$H] RTX, non-radioactive ligands, 0.25 mg/ml bovine serum albumin (Cohn fraction V), and $5×10^4$–$1×10^5$ human capsaicin receptor-transfected HEK-293T cells. The final volume was adjusted to 500 μl (competition binding assays) or 1,000 μl (saturation binding assays) with the buffer described above. Non-specific binding was defined as that occurring in the if presence of 1 μM non-radioactive RTX. For saturation binding, [$^3$H] RTX was added in the concentration range of 7–1,000 pM, using 1 to 2 dilutions. Competition binding assays were performed in the presence of 60 pM [3H] RTX and various concentrations of competing ligands. The binding reaction was initiated by transferring the assay mixtures into a 37° C. water bath and was terminated following a 60 minute incubation period by cooling the tubes on ice. Membrane-bound RTX was separated from free RTX as well as the $α_1$-glycoprotein-bound RTX by pelleting the membranes in a Beckman 12 benchtop centrifuge for 15 minutes at 14,000×g. The radioactivity of membrane-bound RTX was determined by scintillation counting. Equilibrium binding parameters were determined by fitting the Hill equation to the measured values (Szallasi, et al., 1993) with the aid of the computer program Fit™ (Biosoft, Ferguson, Mo.).

Example 5

Calcium Mobilization Assays

A. Response to Capsaicin or Resiniferatoxin

Human capsaicin receptor transfected HEK 293T cells were seeded into 96 well plates and grown to 70–90% confluency. The cells were then washed once with Krebs Ringer solution. Fluo-3 (Molecular Probes, Eugene, Oreg.) calcium sensitive dye (10 ug/mL) was added and incubated with the cells at room temperature for 1 to 2 hours. The 96 well plates were then washed to remove excess dye. Fluorescence response was monitored upon the addition of either 300 nM capsaicin or 30 nM resiniferatoxin by a FLIPR™ plate reader (Molecular Devices, Sunnyvale Calif.) by excitation an 480 nM and emission at 530 nM. Cells transfected with plasmids PT35 and PT44, encoding the full length human capsaicin receptor (SEQ ID NO:1 and SEQ ID NO:2), typically exhibited signals of 5,000–8,000 Arbitrary Fluorescent Light Units in response to agonist.

TABLE II

| Cell Type | Ave Max Response (RFU) |
| --- | --- |
| Wild-Type | 843 |
| PT35 | 7257 |
| PT36 | 805 |
| PT44 | 5529 |

Measurement of intracellular calcium levels in the presence of capsaicin. HEK 293T cells transiently transfected with the indicated plasmids were exposed to 300 nM capsaicin. Intracellular calcium levels were quantitated on the FLIPR plate reader. Data are shown in Relative Fluorescent Units (RFU).

B. Assays for the Identification of Receptor Agonists and Antagonists

The calcium mobilization assay described above may be adapted for identifying test compounds as having agonist or antagonist activity at the human capsaicin receptor.

In order to identify agonist compounds, recombinant cells of the invention are washed and incubated with Fluo-3 dye as described above. A subset of the incubated cells are then exposed to a 1 µM concentration of at least one candidate agonist compound and the fluorescence response is monitored using a FLIPR™ plate reader (Molecular Devices, Sunnyvale, Calif.). Agonist compounds elicit a fluorescence response at least 2-fold that of recombinant cells exposed only to Fluo-3 dye. Preferred agonists elicit a fluorescence response at least 10 fold, and more preferred agonists elicit a fluorescence response at least 20-fold that of recombinant cells exposed only to Fluo-3 dye.

In order to identify antagonist compounds, recombinant cells of the invention are washed an incubated with Fluo-3 dye as described above. One hour prior to measuring the fluorescence signal, a subset of the cells is incubated with a 1 µM concentration of at least one candidate antagonist compound. The fluorescence response upon the subsequent addition of either 300 nM capsaicin or 10 nM resiniferatoxin is monitored using a FLIPR™ plate reader (Molecular Devices). Agonist compounds elicit at least a 2-fold decrease in the fluorescence response relative to that measured in the presence of capsaicin or RTX alone. Preferred antagonist compounds elicit at least a 10 fold, and more preferred antagonists at least a 20-fold decrease in the fluorescence response relative to that measured in the presence of capsaicin or RTX alone.

Example 6

Characterization of Capsaicin Receptors Expressed at High Levels in Cultured Cells

[$^3$H]Resiniferatoxin (RTX) binding and calcium uptake by rat dorsal root ganglion (DRG) neurons show distinct structure-activity relations, suggestive of independent vanilloid receptor (VR) subtypes. To evaluate the hypothesis that binding and calcium uptake detect two distinct classes of VRs in DRG neurons, characterization of RTX binding to the rat capsaicin receptor, VR1, expressed in HEK293 and CHO cells and comparison of the structure-activity relations with those for calcium mobilization was tested. In these binding experiments both typical (capsaicin and olvanil) and novel (isovelleral and scutigeral) vanilloids were included, as well as the competitive VR antagonist capsazepine. Vanilloid binding to HEK293/VR1 cells was compared to that measured in rat DRG neurons expressing native VRs. Calcium mobilization in HEK293/VR1 or CHO/VR1 cells was determined in response to RTX, olvanil, and capsaicin, using a fluorescent method. In addition, capsaicin-induced calcium mobilization in the VR1-transfected cells was measured in the presence of capsazepine or the so-called functional VR antagonist, ruthenium red. Agonist and antagonist potencies determined in the calcium mobilization assays using HEK293/VR1 or CHO/VR1 cells were compared to values measured previously in this laboratory for vanilloid-induced $^{45}$Ca$^{2+}$-uptake by intact rat DRG neurons.

HEK293/VR1 cells and CHO/VR1 cells bound [$^3$H]RTX with affinities of 84 pM and 103 pM, respectively, with a positive cooperativity (Hill numbers were 2.1 and 1.8). These binding parameters are similar to those determined using rat DRG membranes expressing native rat VRs (a $K_d$ of 70 pM and a Hill number of 1.7). The typical vanilloid agonists olvanil and capsaicin inhibited [$^3$H]RTX binding to HEK293/VR1 cells with $K_i$ values of 0.4 µM and 4.0 µM, respectively. The corresponding values in DRG membranes were 0.3 µM and 2.5 µM. HEK293/VR1 cells and DRG membranes also recognized the novel vanilloids isovelleral and scutigeral with similar affinities (18 and 20 µM in HEK293/VR1 cells; 24 and 21 µM in DRGs). The competitive vanilloid receptor antagonist capsazepine inhibited [$^3$H]RTX binding to HEK293/VR1 cells with a $K_i$ value of 6.2 µM, and to DRG membranes with an affinity of 8.6 µM. RTX and capsaicin induced calcium mobilization in HEK293/VR1 cells with EC$_{50}$ values of 4.1 nm and 82 nM, respectively. Thus, the relative potencies of RTX (more potent for binding) and capsaicin (more potent for calcium mobilization) are similar in DRG neurons and cells transfected with VR1. We conclude that VR1 may account for both the ligand binding and calcium uptake observed in rat DRG neurons.

Experimental Procedures

Materials. [$^3$H]Resiniferatoxin (RTX; 37 Ci/mmol) was synthesized by the Chemical Synthesis and Analysis Laboratory, NCI-FCRDC, Frederick, Md. Nonradioactive RTX was purchased from Alexis Corp. (San Diego, Calif.) and capsazepine was from RBI (Natick, Mass.). Olvanil was a generous gift from Procter and Gamble Corp. (Cincinnati, Ohio). Isovelleral and scutigeral were donated by Olov Sterner (Lund Univ., Sweden). All the other chemicals used were purchased from Sigma (St. Louis, Mo.) unless indicated otherwise.

Molecular Biology. A cDNA encoding the rat vanilloid receptor VR1 was cloned from rat dorsal root ganglion (DRG) total RNA by reverse transcription-polymerase chain reaction using primers based on the published nucleotide sequence (Caterina et al., 1997). The forward primer is set forth below as SEQ ID NO:12 and the reverse primer is set forth below as SEQ ID NO:13. A 2.7 kb cDNA was isolated and the nucleotide sequence was verified to be identical to the published sequence, SEQ ID NO:8. This cDNA was subcloned into pcDNA3.1 (Invitrogen, Carlsbad, Calif.) and pTRE (Clontech, Palo Alto, Calif.) for recombinant expression in mammalian cells of the encoded VR1 polypeptide, SEQ ID NO:9.

Cell Culture. The pcDNA3.1 VR1 plasmid was transfected into human embryonic kidney (HEK293) cells using standard methods. These transfected cells were selected for two weeks in media containing G418 (400 µg/ml) and then maintained as a pool of stably transfected cells. The pTRE VR1 plasmid was transfected into Chinese Hamster Ovary (CHO) cells containing the pTet Off Regulator plasmid (Clontech). In these cells, expression of the pTRE plasmid is repressed in the presence of tetracycline but is induced upon removal of the antibiotic. Stable clones were isolated in culture medium containing puromycin 10 (µg/ml) and maintained in medium supplemented with tetracycline (1 µg/ml) Cells utilized for assays were grown in culture medium without antibiotic for 48–72 hours prior to use. For radioligand binding experiments, cells were seeded in T175 cell culture flasks in media without antibiotics and grown to approximately 90% confluency. The flasks were then washed with PBS and harvested in PBS containing 5 mM EDTA. The cells were pelleted by gentle centrifugation and stored at −80° C. until assayed. For calcium mobilization assays, cells were seeded into 96-well plates and grown to 70–90% confluency.

Membrane Preparations. Female Sprague-Dawley rats weighing 200–250 g were euthanized under CO$_2$ anesthesia.

The spinal columns were opened and DRGs were collected from all levels into ice-cold physiological saline. DRGs were disrupted with the aid of a tissue homogenizer in an ice-cold buffer (pH 7.4) containing (in mM) KCl 5, NaCl 5.8, $CaCl_2$ 0.75, $MgCl_2$ 2, sucrose 320, and HEPES 10. Tissue homogenates were first centrifuged for 10 min at 1000×g (4° C.) to remove the nuclear fraction and debris and then the supernatant from the first centrifugation was further centrifuged for 30 min at 35,000×g (4° C.) to obtain a partially purified membrane fraction. Membranes resuspended in the homogenization buffer were stored at −80° C. until assayed.

Radioligand Binding. Binding studies with [3H]RTX were carried out according to a published protocol (Szallasi et al., 1992) in which non-specific RTX binding is reduced by adding bovine alpha, acid glycoprotein (100 μg per tube) after the binding reaction has been terminated. Binding assay mixtures were set up on ice and contained [$^3$H]RTX, non-radioactive ligands, 0.25 mg/ml bovine serum albumin (Cohn fraction V), and either $5×10^4$–$×10^5$ VR1-transfected cells or isolated DRG membranes corresponding to 40 μg of DRG membrane protein. The final volume was adjusted to 500 μl (competition binding assays) or 1,000 μl (saturation binding assays) with the ice-cold HEPES (pH 7.4) buffer solution described above. Non-specific binding was defined as that occurring in the presence of 1 μM non-radioactive RTX. For saturation binding, [$^3$H]RTX was added in the concentration range of 7–1,000 pM, using 1 to 2 dilutions. Competition binding assays were performed in the presence of 30 pM (for DRG membranes) or 60 pM (for VR1-transfected cells) [$^3$H]RTX and various concentrations of competing ligands. The binding reactions were initiated by transferring the assay mixtures into a 37° C. water bath and were terminated following a 60 min incubation period by cooling the tubes on ice. Membrane-bound RTX was separated from free, as well as any alpha$_1$-acid glycoprotein-bound RTX, by pelleting the membranes in a Beckman 12 benchtop centrifuge (15 min, maximal velocity) and the radioactivity determined by scintillation counting. Equilibrium binding parameters were determined by fitting the allosteric Hill equation to the measured values with the aid of the computer program Fit™ (Biosoft, Ferguson, Mo.) as described previously (Szallasi et al., 1993).

Calcium Mobilization Assays. VR1-transfected cells were seeded into 96-well plates and grown to 70–90% confluency. The cells were then washed once with Krebs-Ringer HEPES buffer (25 mM HEPES, 5 nM KCl, 0.96 mM $NaH_2PO_4$, 1 mM $MgSO_4$, 2 mM $CaCl_2$, 5 mM glucose, 1 mM probenecid, pH 7.4) and resuspended and incubated for 1–2 hours in the above buffer supplemented with FLUO3-AM (2.5–10 μg/ml; Teflabs, Austin, Tex. or Molecular Probes, Eugene, Oreg.) at 37° C. in an environment containing 5% $CO_2$. In some experiments (as indicated below in the RESULTS), the Krebs-Ringer HEPES buffer was also supplemented with 1 mg/ml bovine serum albumin (Cohn fraction V). The wells were then washed twice with Krebs Ringer HEPES buffer. Agonist (olvanil, capsaicin, or RTX)-induced calcium mobilization was monitored using either FLUOROSKAN ASCENT (Labsystems, Franklin, Mass.) or FLIPR (Molecular Devices, Sunnyvale, Calif.) instruments. Similarly, varying concentrations of the antagonists ruthenium red or capsazepine were added to cells concurrently with agonist (25–50 nM capsaicin). Fluorescence data were collected to 60–180 seconds and the maximum fluorescence signal was determined. For the capsaicin- and olvanil-induced calcium responses, data obtained between 30 and 60 seconds after agonist application were used to generate the $EC_{50}$ values. Kaleidagraph software (Synergy Software, Reading, Pa.) was utilized to fit the data to the equation:

$$y=a*(1/(1+(b/x)^c))$$

to determine the $EC_{50}$ for the response. In this equation, y is the maximum fluorescence signal, x is the concentration of the agonist or antagonist, a is the $E_{max}$, b corresponds to the $EC_{50}$ or $IC_{50}$ value, and finaly, c is the Hill coefficient.

Results

Rat Capsaicin Receptor VR1-transfected Mammalian Cells (HEK293 and CHO) and Rat DRG Membranes Expressing Native Rat Vanilloid Receptors Bind [$^3$H]RTX with Similar Parameters.

The association of [$^3$H]RTX (60 pM) to VR1 expressed on HEK293 cells was rapid: within 10 min the specific binding attained approximately 90% of its peak value and it then remained on a plateau between 20 min and 60 min of incubation (a single experiment; data not shown). If dissociation was initiated following a 60 min association, it could be fitted to a 1st order decay curve, yielding a dissociation constant of 0.12+/−0.02 min−1 (two determinations; data not shown). Based on these preliminary experiments, an incubation period of 60 min was selected for the equilibrium binding studies.

Figure 1B:
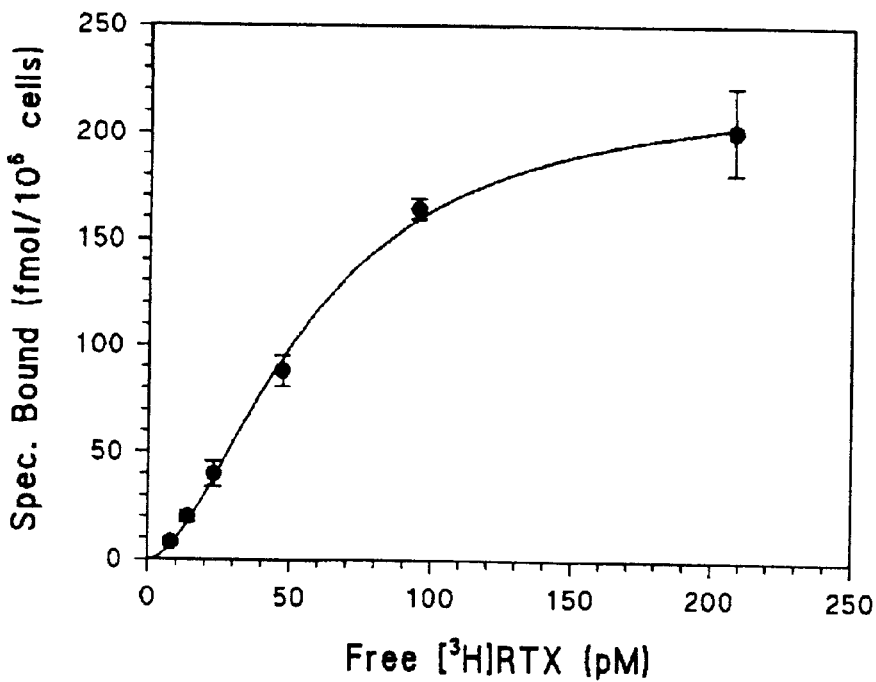
FIG. 1B. Specific binding of [$^3$H]resiniferatoxin to HEK 293 cells transfected stably with a cDNA encoding the rat VR1 (HEK293/VR1 cells). Expanded view of the concentration range from 0–200 pM of the specific binding of [$^3$H]resiniferatoxin to HEK293/VR1 cells. As a result of the cooperativity index approaching 2, the specific binding curve is sigmoidal in this concentration range. Measured values are from FIG. 1A. The binding curve is hypothetical and was computer-generated using the binding parameters from FIG. 1A.
Figure 1C:
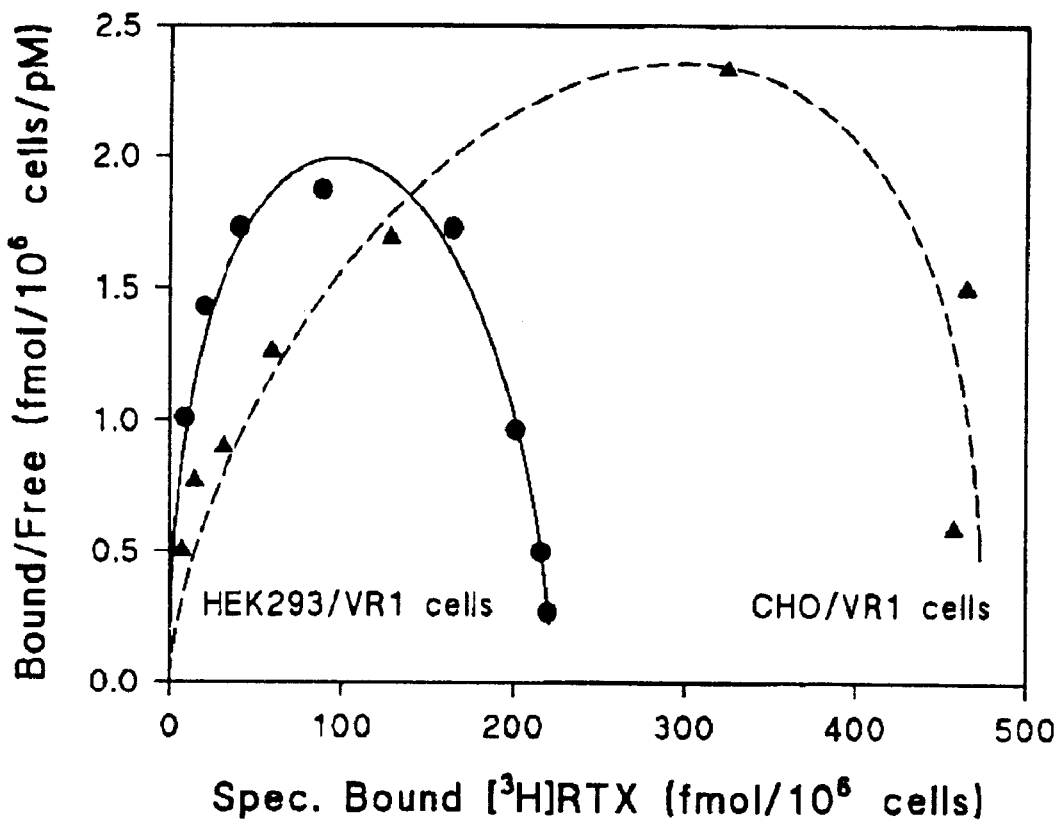
FIG. 1C. Specific binding of [3H]resiniferatoxin to HEK 293 cells transfected stably with a cDNA encoding the rat VR1 (HEK293/VR1 cells). Scatchard plots of specific [3H] resiniferatoxin binding to HEX 293/VR1 cells and CHO/VR1 cells. Filled circles indicate data for HEK293/VR1 cells; data for CHO/VR1 cells are indicated by triangles. The Scatchard plots are convex due to the positive cooperativity of the binding. Also note that the $B_{max}$ value is approximately twice as high in CHO/VR1 as in HEK293/VR1 cells.
Figure 2:
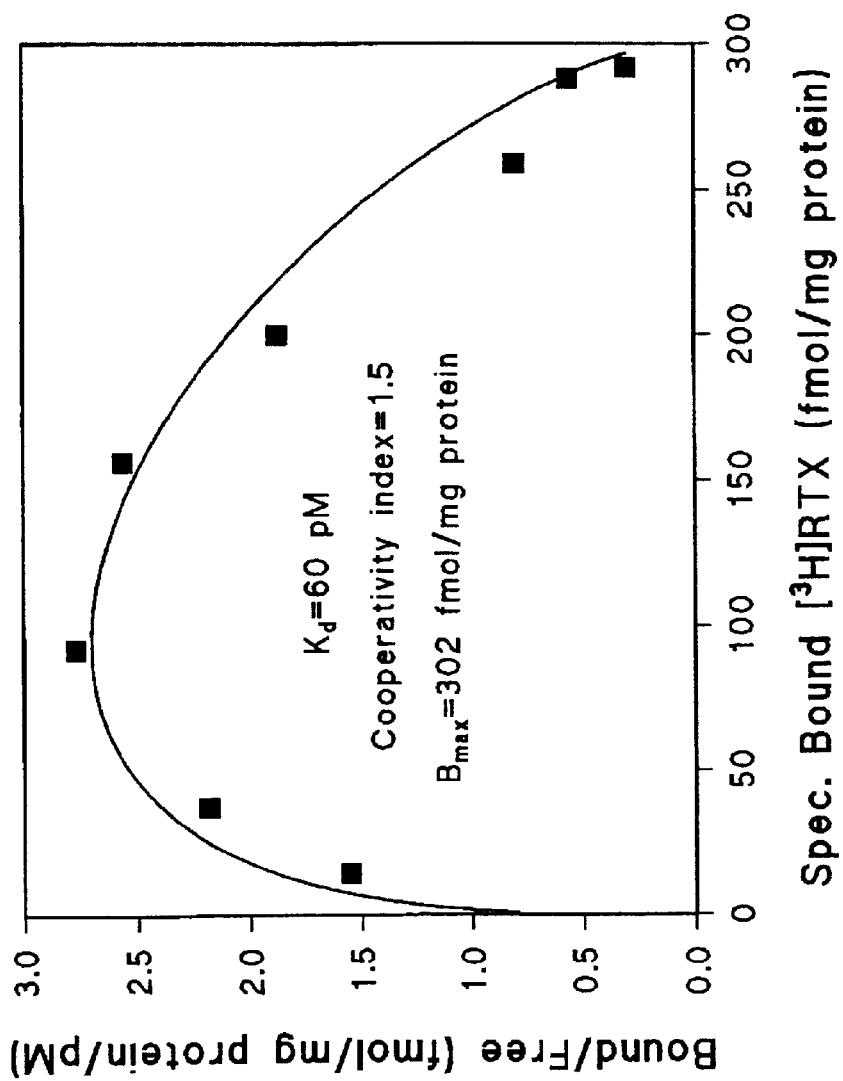
FIG. 2. Scatchard plot of specific [$^3$H] resiniferatoxin binding to rat dorsal root ganglion membranes. Half-maximal binding occurred at a concentration of 60 pM [$^3$H]resiniferatoxin; the maximal receptor density was 302 fmol per one million cells. A Hill coefficient, or cooperativity index, of 1.5 was observed. Compare with FIG. 1C and note that [$^3$H] resiniferatoxin binds to rat dorsal root ganglion membranes expressing native vanilloid receptors and to mammalian cells (HEK293 and CHO) transfected with the cloned rat vanilloid receptor VR1 with similar binding parameters. Results of a single experiment are shown; a second experiment yielded similar results.

[$^3$H]RTX (7–1,000 pM) displayed saturable binding to HEK293/VR1 cells (FIG. 1A). The half-maximal binding occurred at 84+/−11 pM (mean+/−S.E.M.; 4 determinations); at the $K_d$, non-specific binding represented approximately 20% of the total binding (not shown). The saturation binding curve was sigmoidal, indicating positive cooperativity (FIG. 1B). A fit to the allosteric Hill equation yielded a cooperativity index of 2.1+/−0.2 (mean+/−S.E.M.; 4 determinations). This binding behavior results in a convex Scatchard plot (FIG. 1C). The $B_{max}$ value was 250+/−24 fmol/$10^6$ cells (mean+/−S.E.M.; 4 determinations), corresponding to a receptor density of $1.5×10^5$ binding sites per cell. CHO/VR1 cells bound RTX with similar affinity (a $K_d$ of 103+/−13 pM; mean+/−range; 2 determinations) and cooperativity values (a Hill number of 1.9+/−0.1; mean +/−range; 2 experiments). The maximal receptor density was, however, approximately two-fold higher than in the HEK293/VR1 cells (470+/−30 fmol/$10^6$ cells; mean+/−range; 2 determinations) (FIG. 1C). The VR1-transfected cells lines bound RTX with parameters similar not only to each other but also to rat DRG membranes expressing native vanilloid receptors (FIG. 2). DRG membranes bound [$^3$H]RTX with a $K_d$ of 70+/−10 pM and a $B_{max}$ of 290+/−10 fmol/mg protein (mean+/−range; 2 determinations); the cooperativity index was 1.9+/−2 (mean+/−range; 2 determinations).

Although the CHO/VR1 cells provided a higher level of specific binding, HEK293/VR1 cells were chosen for detailed further analysis for a better comparison with the literature (Caterina et al., 1997; Tominaga et al., 1998).

Vanilloid Agonists and the Antagonist Capsazepine Inhibit [$^3$H]RTX Binding by VR1-transfected Mammalian Cells and DRG Membranes, Respectively, with Similar Affinities.

Figure 3A:
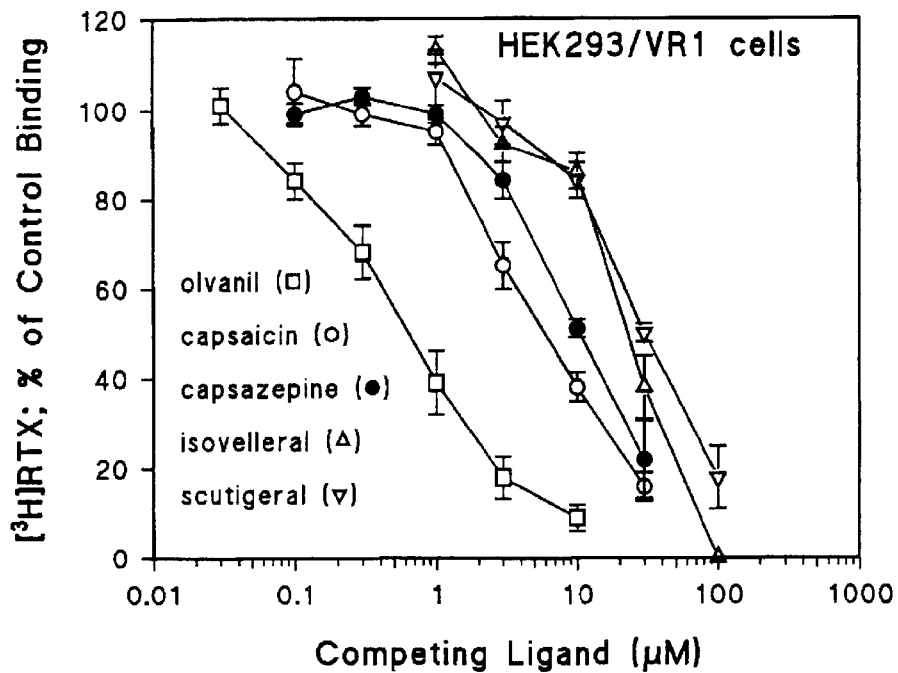
FIG. 3A. Inhibition of specific [$^3$H] resiniferatoxin binding as to HEK 293/VR1 cells by the typical vanilloid agonists olvanil and capsaicin, the novel vanilloids isovelleral and scutigeral, and the competitive vanilloid receptor antagonist capsazepine. Points represent values from 3 to 6 independent determinations; error bars indicate S.E.M. See Example 6, Results, for calculated $K_I$ values.
Figure 3B:
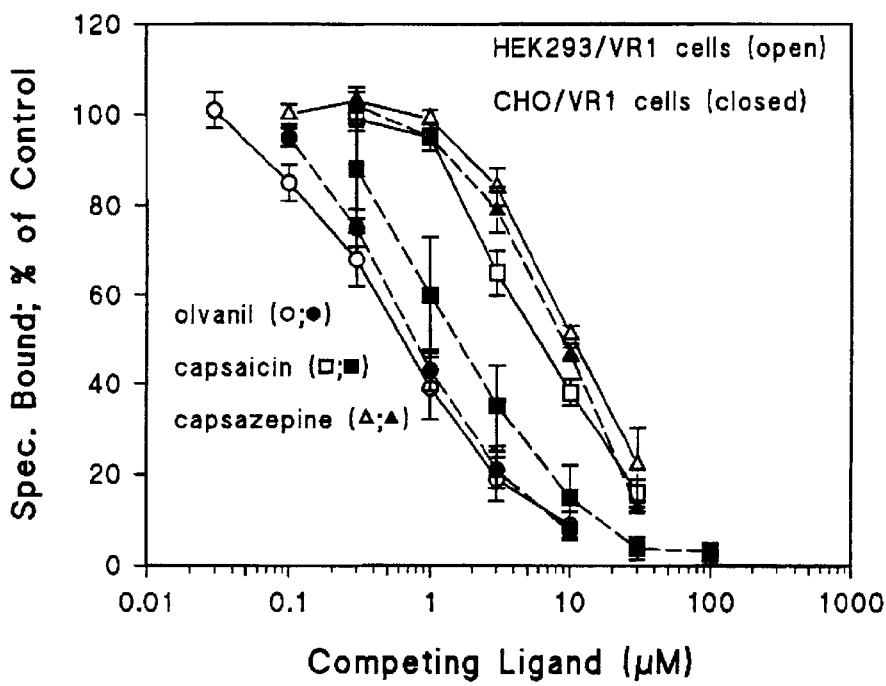
FIG. 3B. Inhibition by olvanil, capsaicin, and capsazepine of specific [3H] resiniferatoxin binding to HEK293/VR1 cells and to CHO/VR1 cells. Open markers indicate data for HEK293/VR1 cells; closed markers indicate data for CHO/VR1 cells. HEK293/VR1 data are from FIG. 3A. For CHO/VR1 cells, points represent mean values of 2 determinations; error bars indicate range.

For the pharmacological characterization of the RTX-recognition site on rat VR1 expressed in HEK293 cells, four agonists (olvanil, capsaicin, isovelleral, and scutigeral) and an antagonist (capsazepine) were selected (FIG. 3). $K_i$ values of the agonists were the following: olvanil, 0.4+/−0.1 μM (n=4); capsaicin, 4.0+/−0.8 μM (n=6); isovelleral, 20+/−4 μM (n=3); and scutigeral, 18+/−3 μM (n=3); all values are mean+/−S.E.M. The competitive antagonist capsazepine inhibited [$^3$H]RTX binding with a $K_i$ of 6.2+/−0.7 μM (mean+/−S.E.M.; 5 experiments). These $K_i$ values are similar to those determined using rat DRG membranes: olvanil, 0.3+/−0.1 μM; capsaicin, 2.5+/−1.1 μM; isovelleral, 24+/−4 μM; scutigeral, 21+/−3 μM; and capsazepine, 8.6+/−3.5 μM (mean+/−S.E.M.; 3 experiments; Table III). The binding affinities of olvanil, capsaicin and capsazepine were also determined using CHO/VR1 cells: $K_i$ values were 0.26+/−0.5 µM, 1.3+/−0.4 µM, and 6.6+/−1.4 µM, respectively (mean+/−range; 2 determinations; TABLE III).

TABLE III

| Ligand | Rat dorsal root ganglion neurons | | CHO/VR1 cells | |
|---|---|---|---|---|
| | Binding affinity (nM) | $^{45}Ca^{2+}$− uptake ($EC_{50}$, nM)* | Binding affinity (nM) | $Ca^{2+}$− mobilization ($EC_{50}$, nM) |
| Resiniferatoxin | 0.07 | 1 | 0.13 | 1.4 |
| capsaicin | 2,500 | 340 | 1,700 | 38 |
| olvanil | 300 | 170** | 260 | 216 |
| capsazepine*** | 8,600 | 271 | 5,100 | 140 (1,100) |
| Ruthenium red | no effect | 790 | no effect | 210 |

Values are means of at least 4 independent determinations.
*From Ács, G. et al. (1996) Mol. Brain Res. 35: 173–182.
**From Walpole, C. S. J. and Wrigglesworth, R. (1993) in Capsaicin in the Study of Pain
***For capsazepine, $K_i$ values are given; the values in parenthesis (1,100 nM) were obtained in the absence of bovine serum albumin, 1 mg/ml.

Characterization of Rat Capsaicin Receptor VR1-transfected Mammalian Cells in the Calcium Mobilization Assay Using Various Vanilloid Compounds.

Figure 4A:
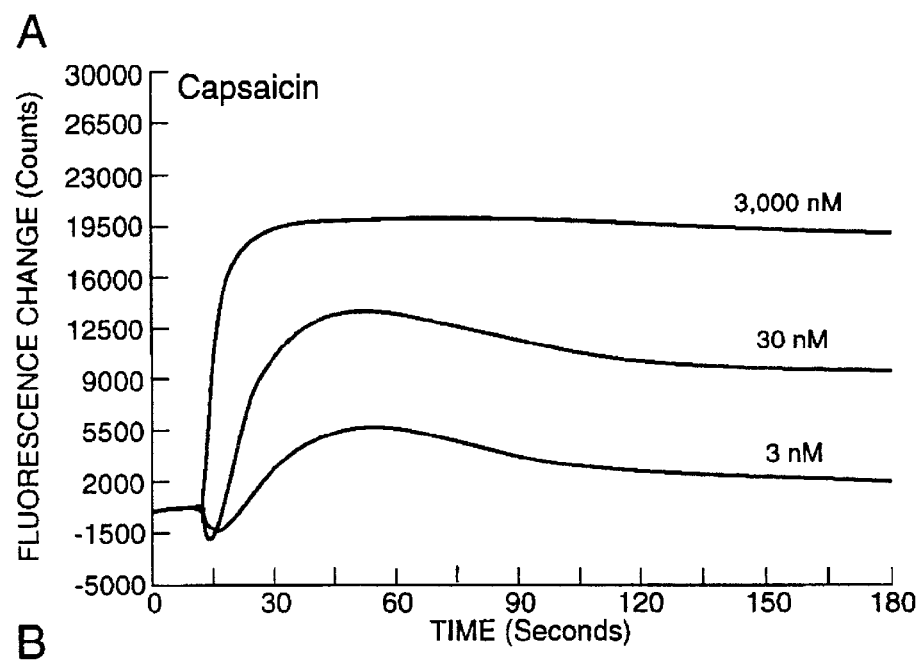
FIG. 4A. Time dependence of capsaicin and RTX-evoked calcium mobilization in CHO/VR1 cells. Time dependence of capsaicin-evoked calcium mobilization in CHO/VR1 cells in response to 3 nM, 30 nM and 3,000 nM capsaicin.
Figure 4B:
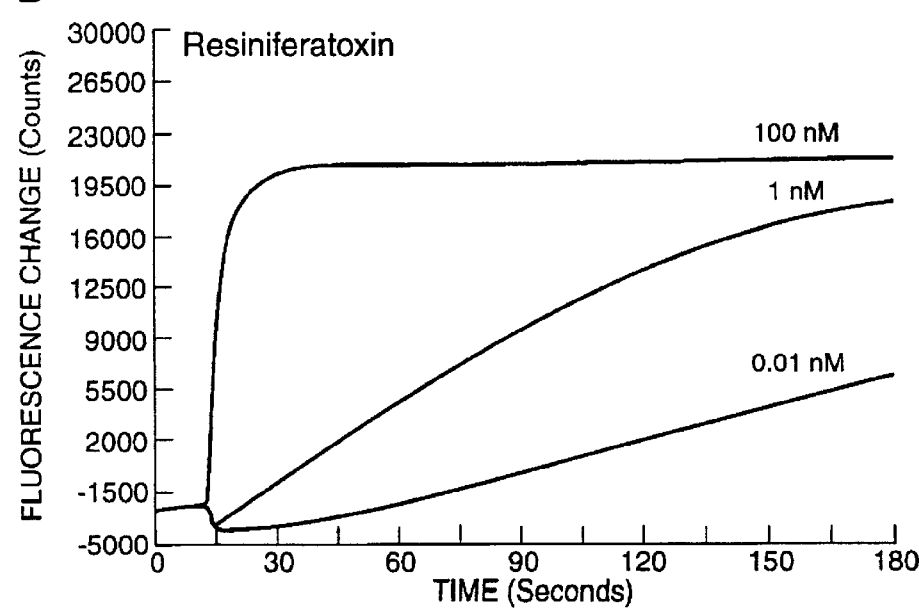

Capsaicin induced calcium mobilization in HEK293/VR1 cells and CHO/VR1 cells with $EC_{50}$ values of 82+/−17 nM (mean+/−S.E.M.; n=4) and 38+/−16 nM (mean+/−S.E.M.; n=5), respectively. RTX was more than an order of a magnitude more potent in both cell lines; $EC_{50}$ values were 4.1+/−1.3 nM in HEK293/VR1 cells (mean+/−S.E.M.; n=5), and 1.4+/−0.8 nM in CHO/VR1 cells (mean+/−S.E.M.; n=4). Capsaicin and RTX differed not only in potency in the calcium mobilization assay, but also in the kinetics of the response as shown by FIG. 4. Using 30 nM capsaicin, a concentration close to the $EC_{50}$ in CHO/VR1 cells, led to rapid calcium mobilization responses: the maximal fluorescence change occurred within 30 sec. (30 µM capsaicin) to 50 sec. (3 nM capsaicin) By contrast, RTX-evoked calcium mobilization became detectable only after an initial delay (compare FIG. 4A and FIG. 4B). The calcium mobilization response to capsaicin achieved its peak value within 1 min. and then started to decline, suggestive of the development of tachyphylaxis or due to some other aspect of channel gating (FIG. 4A). By contrast, unless high RTX concentrations were used (such as 100 nM, a value almost 100-fold higher than the $EC_{50}$), resiniferatoxin application resulted in slowly developing but persistent calcium currents. Calcium mobilization in response to 1 nM RTX increased steadily over a 3 min. period after challenge, approaching the maximal response evoked by 100 nM RX (FIG. 4B) This difference between the kinetics of capsaicin-induced and RTX-induced responses, however, disappeared when high, supramaximal doses were used (30 uM capsaicin or 100 nM RTX; compare FIG. 4A and FIG. 4B). Olvanil evoked the calcium response in CHO/VR1 cell with a potency of 22+/−6 nM (mean+/−S.E.M.; n=7). The time-course of the olvanil-induced calcium mobilization response was similar to that triggered by capsaicin (not shown). When 25 nM capsaicin was administered to evoke calcium mobilization, capsazepine inhibited this response with an $IC_{50}$ value of 2.4+/−0.5 uM (mean+/−S.E.M.; n=6). This value was, however, shifted by almost an order of magnitude in the presence of 1 mg/ml bovine serum albumin to yield an $IC_{50}$ value of 0.33+/−0.03 uM (mean+/−S.E.M.; n=5). For the other vanilloids tested in this study, the presence or absence of bovine serum albumin had no detectable influence on the calcium mobilization potency. With an $IC_{50}$ of 210+/−30 NM (mean+/−S.E.M.; n=7), the functional antagonist ruthenium red was similar in potency to capsazepine in ability to prevent calcium mobilization by capsaicin.

A further discussion of these results can be found in Szallasi et al., 1999.

Although the invention has been described in connection with specific preferred embodiments, it should be understood that the invention as claimed should not be unduly limited to such specific embodiments. Various modifications of the described modes for carrying out the invention that are obvious to those skilled in the relevant arts are within the scope of the invention. It is also to be understood that the terminology used herein is for the purpose of describing particular embodiments only and is not intended to limit the scope of the present invention, which will be limited only by the appended claims.

REFERENCES CITED

Ács, G., Lee, J., Marquez, V. E., and Blumberg, P. M. (1996) Mol. Brain Res. 35: 173–182.

Bevan, S. and Geppetti, P. (1994) Trends Neurosci. 17: 509–512.

Caterina, M. J., Schumacher, M. A., Tominaga, M., Rosen, T. A., Levine, J. D. and Julius, D., (1997) Nature 389: 816–824.

Caterina, M. J., Rosen, T. A., Tominaga, M., Brake, A. J., and Julius, D. (1999) Nature 398: 436–441.

Chou, P. Y. and Fasman G. D. (1974) Biochemistry 13: 222–244.

Clapham, D. E. (1996) Neuron 16: 1069–1072.

Julius, D., Caterina, M., and Brake, A. WIPO-PCT publication No. WO 99/09140.

Kirshstein, T., Busselberg, D., Treede, R. D. (1997) Neurosci. Lett. 231(1): 33–36.

Kress, M., Fetzer, S., Reeh, P. W. and Vyklicky (1996) Neurosci. Lets. 211: 5–8.

Kress, M. and Reeh, P. W. (1996) in Neurobiology of Nociceptors (Cervero, F. and Belmonte, C., eds.), 258–297, Oxford University Press.

Muench, G., Walker, P., Shine, J. and Herzog, H. (1995) Recept. Channels 3(4): 291–297.

Schulz, G. E. and Schirmer, R. H. (1990) in Principles of Protein Structure, Charles Cantor, editor, p. 14–16, Springer-Verlag, NY Oh, U., Hwang, S. W. and Kim, D. (1996) J. Neurosci. 16: 1659–1667.

Szallasi, A. and Blumberg, P. M. (1989) Neuroscience 30: 515–520.

Szallasi, A., Lewin, N. E. and Blumberg, P. M. (1992) J. Pharmacol. Exp. Ter. 262: 883–888.

Szallasi, Lewin, N. E. and Blumberg, P. M. (1993) J. Pharmacol. Exp. Ther. 266: 678–683.

Szallasi, A., Blumberg, P. M., Annicelli, L. L., Krause, J., and Cortright, D. N. (1999) Mol. Pharmacol. 56(3): 581–7.

Szolcsanyi, J and Jancso-Gabor, A. (1975) Drug Res. 25: 1877–1881.

Szolcsanyi, J and Jancso-Gabor, A. (1976) Drug Res. 26: 33–37.

Tominaga, M., Caterain, M. J., Malmber, A. B., Rosen, T. A., Gilbert, H., Skinner, K., Raumann, B. E., Basbaum, A. I. and Julius, D. (1998) Neuron 21: 531–543.

Walpole, C. S. J. and Wrigglesworth, R. (1993) in Capsaicin in the Study of Pain (Wood, J. N., ed.) pp. 63–82, Academic Press, San Diego.

Zeilhofer, H. U., Kress, M. and Swandulla, D. (1997) J. Physiol. 503: 67–78.

What is claimed is:

1. An isolated nucleic acid molecule encoding the amino acid sequence of SEQ ID NO:5.

2. A nucleic acid vector for recombinant expression of a human capsaicin receptor comprising a nucleic acid sequence encoding the amino acid sequence of SEQ ID NO:4, operatively linked to a nucleic acid sequence comprising at least one heterologous regulatory element in the appropriate orientation for expression.

3. The vector of claim 2, wherein the vector is a plasmid vector.

4. The vector of claim 2, herein the vector is a viral vector.

5. A recombinant cell comprising the vector of claim 2.

6. The recombinant cell of claim 5, wherein the recombinant cell is a bacterial cell.

7. The recombinant cell of claim 5, wherein the recombinant cell exhibits capsaicin agonist binding activity that significantly greater to the $p \leq 0.05$ level, as measured using a parametric test of statistical significance, than that exhibited by the host cell.

8. The recombinant cell of claim 7, wherein the recombinant cell is an insect cell.

9. The recombinant cell of claim 7, wherein the cell is an amphibian cell.

10. The recombinant cell of claim 9, wherein the amphibian cell is an oocyte.

11. The recombinant cell of claim 7, wherein the cell is a mammalian cell.

12. The recombinant cell of claim 11, wherein the cell is a HEK 293 cell.

13. An isolated nucleic acid molecule encoding the amino acid sequence of SEQ ID NO:4.

14. A nucleic acid vector for recombinant expression of a human capsaicin receptor comprising a nucleic acid sequence encoding the amino acid sequence of SEQ ID NO:5, operatively linked to a nucleic acid sequence comprising at least one heterologous regulatory element in the appropriate orientation for expression.

15. A recombinant cell comprising the vector of claim 14.

* * * * *